(12) United States Patent
Gerecht et al.

(10) Patent No.: US 11,332,717 B2
(45) Date of Patent: May 17, 2022

(54) THREE-DIMENSIONAL VASCULAR NETWORK ASSEMBLY FROM INDUCED PLURIPOTENT STEM CELLS

(71) Applicant: THE JOHNS HOPKINS UNIVERSITY, Baltimore, MD (US)

(72) Inventors: Sharon Gerecht, Severna Park, MD (US); Xin Yi Chan, Baltimore, MD (US); Quinton Smith, Albuquerque, NM (US); Yu-I Shen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 164 days.

(21) Appl. No.: 15/746,477

(22) PCT Filed: Jul. 21, 2016

(86) PCT No.: PCT/US2016/043231
§ 371 (c)(1),
(2) Date: Jan. 22, 2018

(87) PCT Pub. No.: WO2017/015415
PCT Pub. Date: Jan. 26, 2017

(65) Prior Publication Data
US 2018/0216063 A1    Aug. 2, 2018

Related U.S. Application Data

(60) Provisional application No. 62/195,644, filed on Jul. 22, 2015.

(51) Int. Cl.
| | | |
|---|---|---|
| *C12N 5/071* | (2010.01) | |
| *A61K 9/00* | (2006.01) | |
| *A61K 9/06* | (2006.01) | |
| *A61K 47/36* | (2006.01) | |
| *A61K 47/42* | (2017.01) | |
| *A61K 35/00* | (2006.01) | |
| *A61K 35/545* | (2015.01) | |
| *A61P 31/02* | (2006.01) | |
| *A61L 27/24* | (2006.01) | |

(52) U.S. Cl.
CPC ............ *C12N 5/069* (2013.01); *A61K 9/0024* (2013.01); *A61K 9/06* (2013.01); *A61K 35/00* (2013.01); *A61K 35/545* (2013.01); *A61K 47/36* (2013.01); *A61K 47/42* (2013.01); *A61L 27/24* (2013.01); *A61P 31/02* (2018.01); *C12N 2500/44* (2013.01); *C12N 2501/165* (2013.01); *C12N 2501/727* (2013.01); *C12N 2501/999* (2013.01); *C12N 2506/45* (2013.01); *C12N 2533/80* (2013.01)

(58) Field of Classification Search
CPC ............... C12N 5/069; C12N 2500/44; C12N 2501/165; C12N 2501/727; C12N 2501/999; C12N 2506/45; C12N 2533/80; A61P 31/02; A61K 9/0024; A61K 9/06; A61K 35/00; A61K 35/545; A61K 47/36; A61K 47/42; A61L 27/24
See application file for complete search history.

(56) References Cited

U.S. PATENT DOCUMENTS

| 8,377,555 B2 | 2/2013 | Mohtadi et al. |
| 2014/0273220 A1 | 9/2014 | Gerecht et al. |
| 2014/0356455 A1 | 12/2014 | Reijo Pera et al. |
| 2018/0092941 A1 | 4/2018 | Gerecht et al. |

FOREIGN PATENT DOCUMENTS

| WO | 2008029401 A1 | 3/2009 |
| WO | 2011025755 A1 | 3/2011 |
| WO | 2015054526 A2 | 4/2015 |

OTHER PUBLICATIONS

"Single Cell Passaging Methods" by ThermoFisher, pp. 1-4, publically available Feb. 25, 2015.*
Lian et al., Stem Cell Reports, vol. 3, 804-816, Nov. 11, 2014.*
Georgescu et al., European Journal of Pharmacology, 669: 1-6, 2011.*
Pagiatakis, et al., "A Novel RhoA/ROCK-CPI-17-MEF2C Signaling Pathway Regulates Vascular Smooth Muscle Cell Gene Expression" Journal of Biological Chemistry. 2012;287:8361-8370.
Steed, et al., Guidelines for the treatment of diabetic ulcers. Wound repair and regeneration : official publication of the Wound Healing Society [and] the European Tissue Repair Society. 2006;14:680-692.
Zorlutuna, et al., Microfabricated biomaterials for engineering 3D tissues. Adv Mater. Apr. 10, 2012,24(14):1782-804.
Han, et al., Nitric oxide releasing nanoparticles are therapeutic for *Staphylococcus aureus* abscesses in a murine model of infection. PLoS One. Nov. 12, 2009;4(11):e7804.
Joo, et al., ROCK suppression promotes differentiation and expansion of endothelial cells from embryonic stem cell-derived Flk1 (+) mesodermal precursor cells. Blood. Sep. 27, 2012;120(13):2733-44.
Maehr, et al., Generation of pluripotent stem cells from patients with type 1 diabetes. Proc Natl Acad Sci USA. Sep. 15, 2009; 106(37):15768-73.
Vo, et al., Smooth-muscle-like cells derived from human embryonic stem cells support and augment cord-like structures in vitro. Stem Cell Rev. Jun. 2010;6(2):237-47.
Khetan, et al., Sequential crosslinking to control cellular spreading in 3-dimensional hydrogels. Soft Matter. Feb. 2009;5:1601-1606.

(Continued)

*Primary Examiner* — Thaian N. Ton
(74) *Attorney, Agent, or Firm* — Venable LLP; Keith G. Haddaway

(57) ABSTRACT

Early vascular cells (EVCs), including endothelial cells and pericytes, are generated from hiPSCs. Unlike the isolated endothelial progenitor cells, the differentiated ECs mature and are functional. When encapsulated in synthetic hydrogel, EVCs respond to matrix cues and self-assembled to form three-dimensional EVCs. Moreover, these EVCs respond to hypoxic microenvironment and undergo vasculogenesis to form complex 3D networks.

18 Claims, 18 Drawing Sheets

Specification includes a Sequence Listing.

(56) References Cited

OTHER PUBLICATIONS

Khetan, et al., Patterning network structure to spatially control cellular remodeling and stem cell fate within 3-dimensional hydrogels. Biomaterials. Nov. 2010;31(32):8228-34.

Kusuma, S., et al., "Self-organized vascular networks from human pluripotent stem cells in a synthetic matrix", PNAS, Jul. 30, 2013, vol. 110, No. 31, pp. 12601-12606.

Kusuma, S., et al., "Characterizing human pluripotent stem cell derived vascular cells for tissue engineering applications", Stem Cells and Development, vol. 24, No. 4 (2015).

Liao, J., "Rho Kinase (ROCK) Inhibitors" J Cardiovasc Pharmacol. Jul. 2007 ; 50(1): 17-24. doi:10.1097/FJC.0b013e318070d1bd.

Massague, J., "TGFβ signalling in context" Nature (2012) vol. 13, pp. 616-630.

Hanjaya-Putra, et al., Controlled activation of morphogenesis to generate a functional human microvasculature in a synthetic matrix. Blood. Jul. 21, 2011;118(3):804-15.

Davis, et al., Endothelial extracellular matrix: biosynthesis, remodeling, and functions during vascular morphogenesis and neovessel stabilization. Circ Res. Nov. 25, 2005;97(11):1093-107.

Jin, et al., Enzyme-mediated fast in situ formation of hydrogels from dextran-tyramine conjugates. Biomaterials. Jun. 2007;28(18):2791-800.

Cuchiara, et al., Integration of Self-Assembled Microvascular Networks with Microfabricated PEG-Based Hydrogels. Adv Funct Mater. Nov. 7, 2012;22(21):4511-4518.

Khetan, et al., Degradation-mediated cellular traction directs stem cell fate in covalently crosslinked three-dimensional hydrogels. Nat Mater. May 2013; 12(5): 458-465.

Deforest, et al., Sequential click reactions for synthesizing and patterning three-dimensional cell microenvironments. Nat Mater. Aug. 2009;8(8):659-64.

Nguyen-Ngoc, et al., Mammary ductal elongation and myoepithelial migration are regulated by the composition of the extracellular matrix. J Microsc. Sep. 2013;251(3):212-23.

Murphy, et al., Deaths: Final data for 2010. National vital statistics reports : from the Centers for Disease Control and Prevention, National Center for Health Statistics, National Vital Statistics System. 2013;61:1-117.

Resnick, et al., Diabetes and cardiovascular disease. Annual review of medicine. 2002;53:245-267.

Wilson, Diabetes mellitus and coronary heart disease. American journal of kidney diseases : the official journal of the National Kidney Foundation. 1998;32:S89-100.

Kota, et al., Aberrant angiogenesis:The gateway to diabetic complications. Indian journal of endocrinology and metabolism. 2012;16:918-930.

Simons, Angiogenesis, arteriogenesis, and diabetes: Paradigm reassessed? Journal of the American College of Cardiology. 2005;46:835-837.

Bento, et al., Regulation of hypoxia-inducible factor 1 and the loss of the cellular response to hypoxia in diabetes. Diabetologia. 2011;54:1946-1956.

Caballero, et al., Ischemic vascular damage can be repaired by healthy, but not diabetic, endothelial progenitor cells Diabetes. 2007;56:960-967.

Kusuma, et al., Self-organized vascular networks from human pluripotent stem cells in a synthetic matrix. Proceedings of the National Academy of Sciences of the United States of America. 2013;110:12601-12606.

Seifu, et al., Small-diameter vascular tissue engineering. Nature reviews. Cardiology. 2013;10:410-421.

Sun, et al., Vascular regeneration: Engineering the stem cell microenvironment. Regenerative medicine. 2009;4:435-447.

Leeper, et al., Stem cell therapy for vascular regeneration: Adult, embryonic, and induced pluripotent stem cells. Circulation. 2010;122:517-526.

Cho, et al., Improvement of postnatal neovascularization by human embryonic stem cell derived endothelial-like cell transplantation in a mouse model of hindlimb ischemia. Circulation. 2007;116:2409-2419.

Huang, et al., Embryonic stem cell-derived endothelial cells engraft into the ischemic hindlimb and restore perfusion. Arteriosclerosis, thrombosis, and vascular biology. 2010;30:984-991.

Asahara, et al., Isolation of putative progenitor endothelial cells for angiogenesis. Science. 1997;275:964-967.

Li, et al., Functional and transcriptional characterization of human embryonic stem cell-derived endothelial cells for treatment of myocardial infarction. PloS one. 2009;4:e8443.

Loomans, et al., Differentiation of bone marrow-derived endothelial progenitor cells is shifted into a proinflammatory phenotype by hyperglycemia. Molecular Medicine. 2009;15:152-159.

Menegazzo, et al., Endothelial progenitor cells in diabetes mellitus. Biofactors. 2012;38:194-202.

Tepper, et al., Human endothelial progenitor exhibit impaired proliferation, cells from type ii diabetics adhesion, and incorporation into vascular structures. Circulation. 2002;106:2781-2786.

Yu, et al., Induced pluripotent stem cell lines derived from human somatic cells. Science. 2007;318:1917-1920.

Takahashi, et al., Induction of pluripotent stem cells from adult human fibroblasts by defined factors. Cell. 2007;131:861-872.

Mattout, et al., Global epigenetic changes during somatic cell reprogramming to ips cells. J Mol Cell Biol. 2011;3:341-350.

Kusuma, et al., Low oxygen tension enhances endothelial fate of human pluripotent stem cells. Arteriosclerosis, thrombosis, and vascular biology. 2014;34:913-920.

Kusuma, et al., Characterizing human pluripotent-stem-cell-derived vascular cells for tissue engineering applications. Stem cells and development. 2015;24:451-458.

Armulik, et al., Pericytes: Developmental, physiological, and pathological perspectives, problems, and promises. Developmental Cell. 2011;21:193-215.

Chou, et al., Efficient human ips cell derivation by a non-integrating plasmid from blood cells with unique epigenetic and gene expression signatures. Cell Res. 2011;21:518-529.

Cheng, et al., Low incidence of DNA sequence variation in human induced pluripotent stem cells generated by nonintegrating plasmid expression. Cell Stem Cell. 2012;10:337-344.

Watanabe, et al., A rock inhibitor permits survival of dissociated human embryonic stem cells. Nature biotechnology. 2007;25:681-686.

Gage, et al., Initial cell seeding density influences pancreatic endocrine development during in vitro differentiation of human embryonic stem cells. PloS one. 2013;8:e82076.

Davis, et al., Molecular basis for endothelial lumen formation and tubulogenesis during vasculogenesis and angiogenic sprouting. International review of cell and molecular biology. 2011;288:101-165.

Capla, et al., Diabetes impairs endothelial progenitor cell-mediated blood vessel formation in response to hypoxia. Plastic and reconstructive surgery. 2007;119:59-70.

Park, et al., Hypoxia-inducible hydrogels. Nature communications. 2014;5:4075.

Au, et al., Differential in vivo potential of endothelial progenitor cells from human umbilical cord blood and adult peripheral blood to form functional long-lasting vessels. Blood. 2008;111:1302-1305.

Au, et al., Bone marrow-derived mesenchymal stem cells facilitate engineering of long-lasting functional vasculature. Blood. 2008;111:4551-4558.

Koike, et al., Tissue engineering: Creation of long-lasting blood vessels. Nature. 2004;428:138-139.

Wang, et al., Endothelial cells derived from human embryonic stem cells form durable blood vessels in vivo. Nature biotechnology. 2007;25:317-318.

Holy, et al., Engineering three-dimensional bone tissue in vitro using biodegradable scaffolds: Investigating initial cell-seeding density and culture period. Journal of biomedical materials research. 2000;51:376-382.

Ghosh, et al., Cell density-dependent transcriptional activation of endocrine-related genes in human adipose tissue-derived stem cells. Experimental cell research. 2010;316:2087-2098.

(56) References Cited

OTHER PUBLICATIONS

Chen, et al., Actin-myosin contractility is responsible for the reduced viability of dissociated human embryonic stem cells. Cell Stem Cell. 2010;7:240-248.
Yang, et al., The rhoa-rock-pten pathway as a molecular switch for anchorage dependent cell behavior. Biomaterials. 2012;33:2902-2915.
Li, et al., Regulation of pten by rho small gtpases. Nature Cell Biology. 2005;7:399-U342.
Song, et al., The functions and regulation of the pten tumour suppressor. Nature Reviews Molecular Cell Biology. 2012;13:283-296.
Shiojima, et al., Role of akt signaling in vascular homeostasis and angiogenesis. Circ Res. 2002;90:1243-1250.
Castellani, et al.. Fine regulation of rhoa and rock is required for skeletal muscle differentiation. Journal of Biological Chemistry. 2006;281:15249-15257.

\* cited by examiner

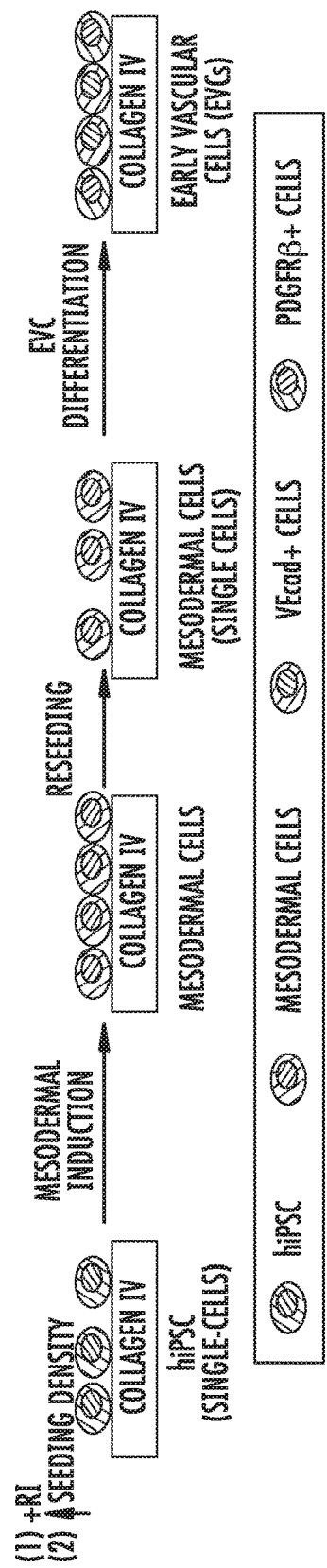
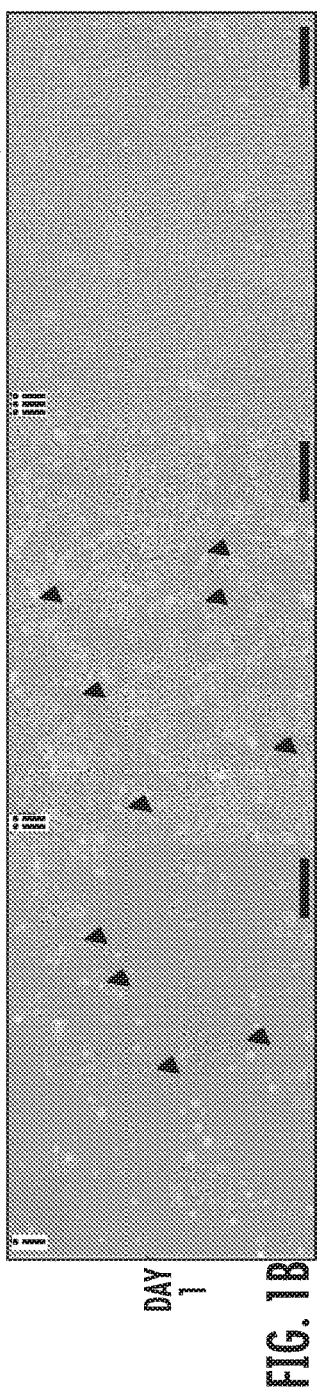
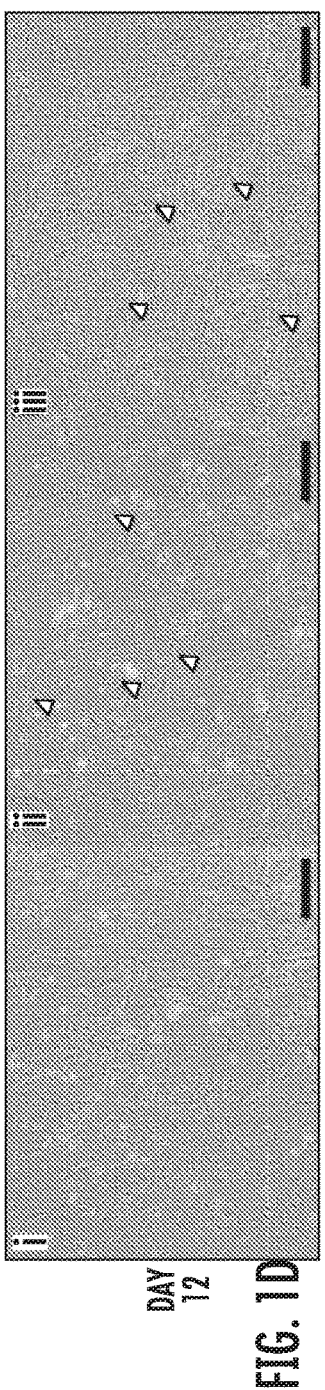
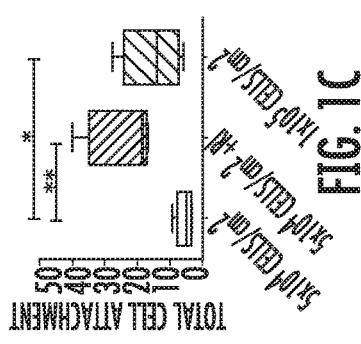
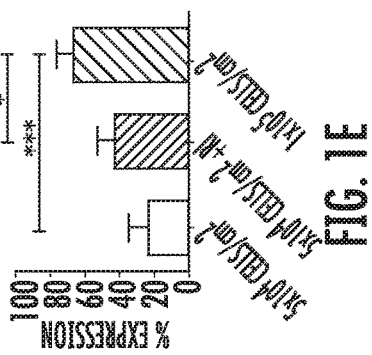

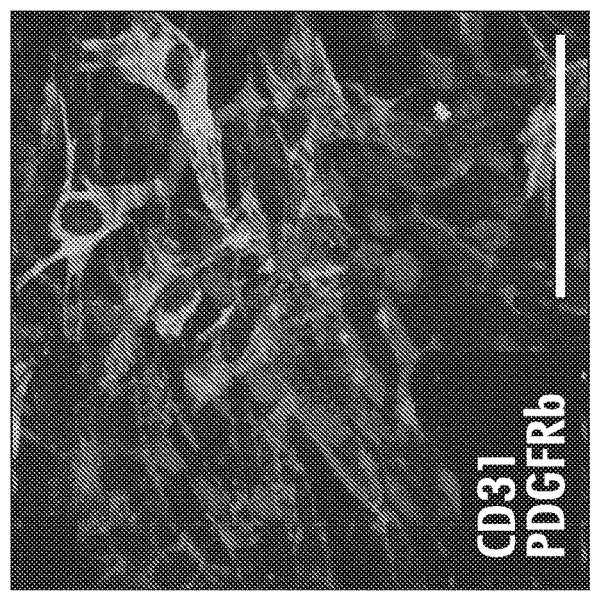
FIG. 3A
FIG. 3C
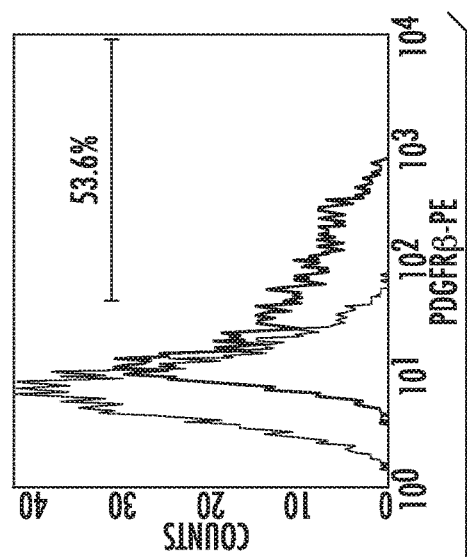
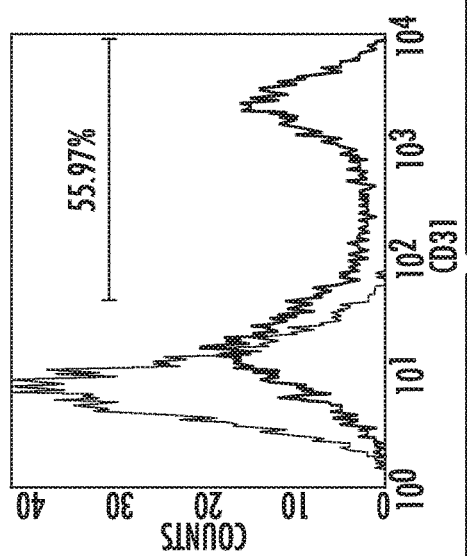
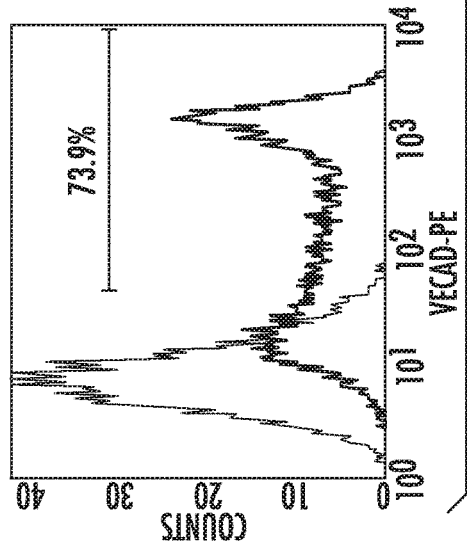
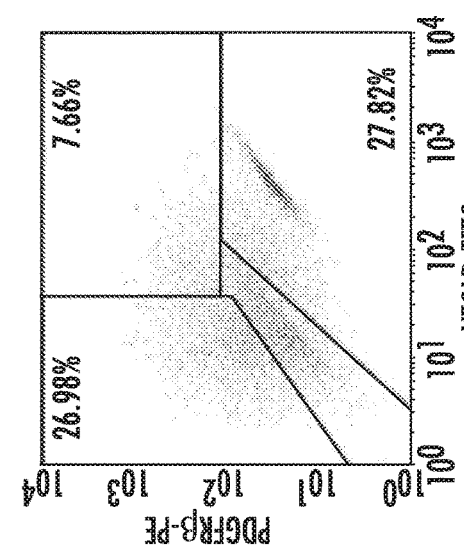
FIG. 3B
FIG. 3D

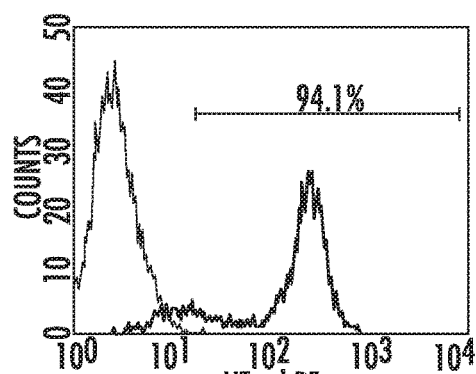
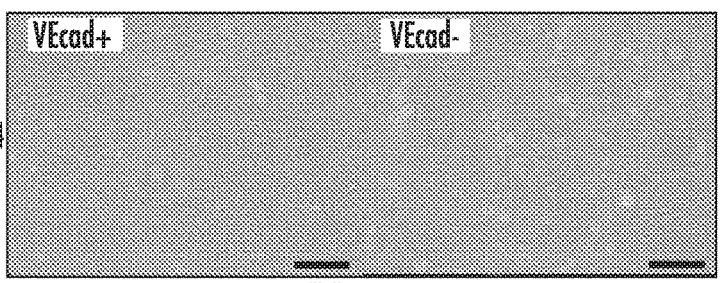
FIG. 4A
FIG. 4B
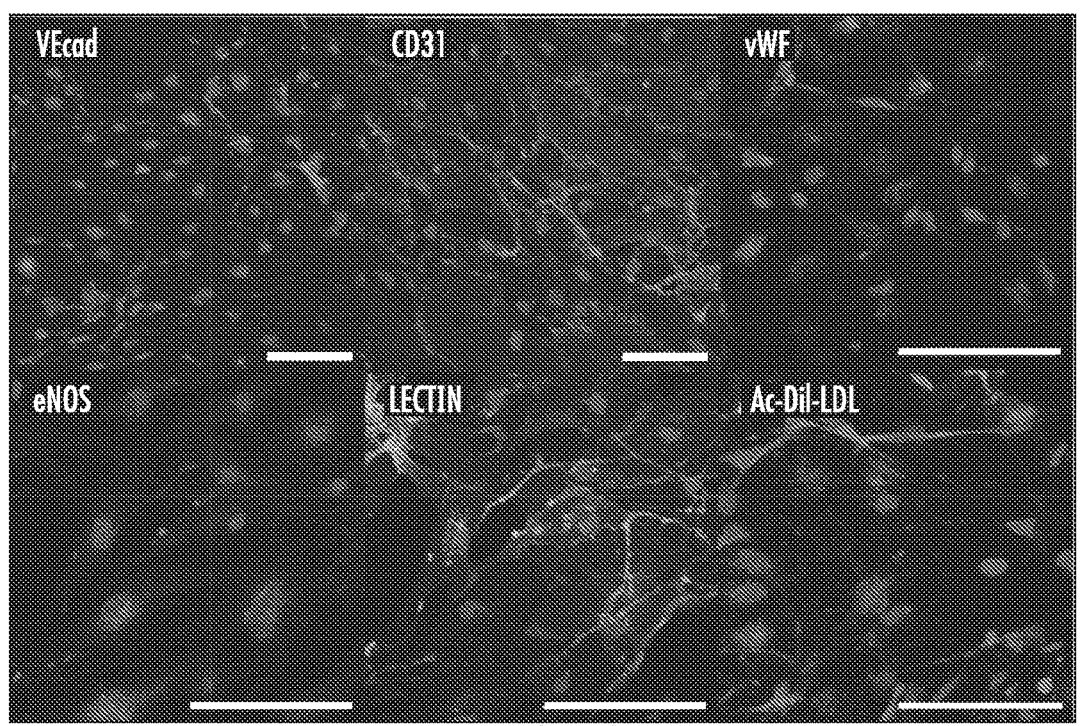
FIG. 4C
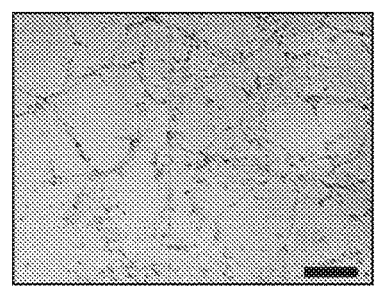
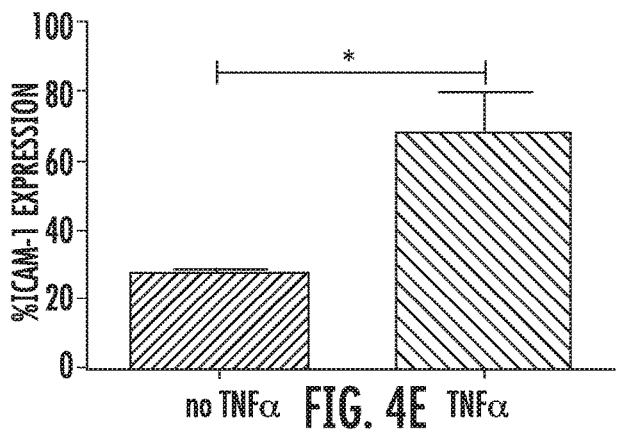
FIG. 4D
FIG. 4E

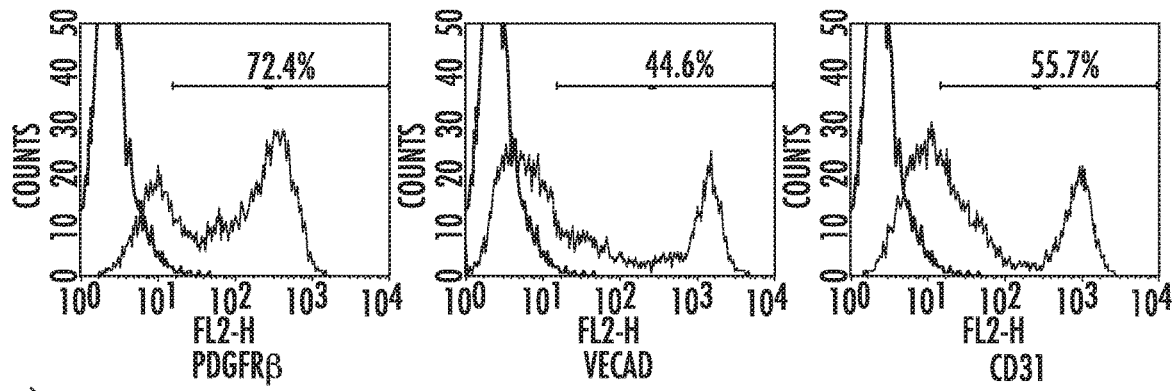
FIG. 9A
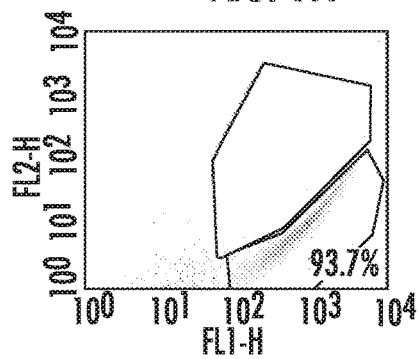
FIG. 9Bi
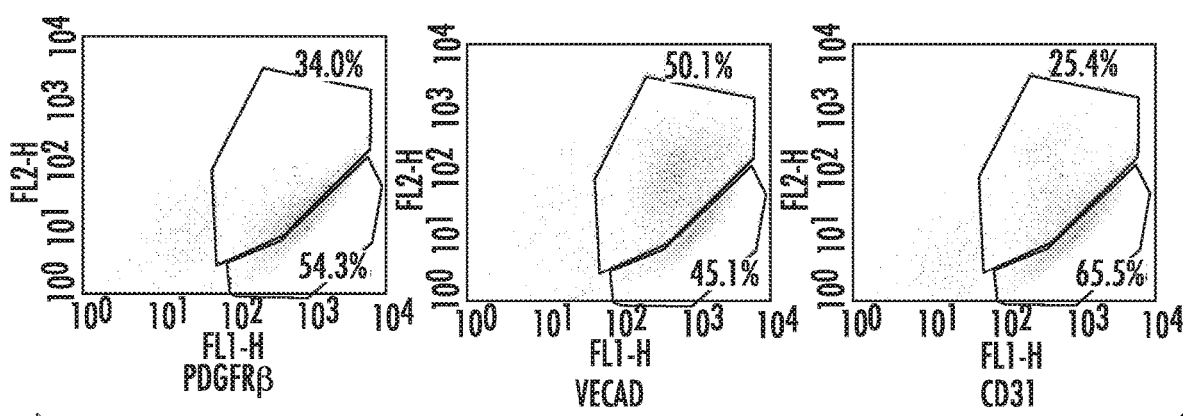
FIG. 9Bii

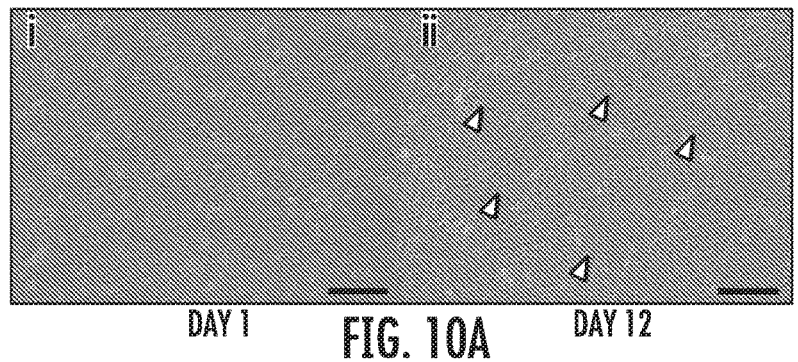
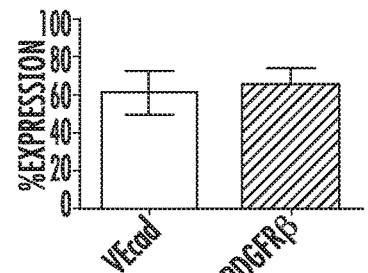
FIG. 10A  FIG. 10B
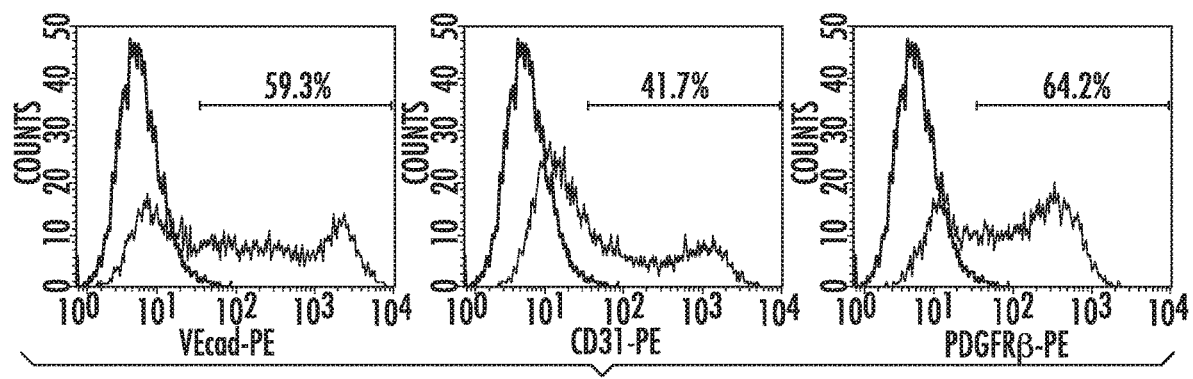
FIG. 10C
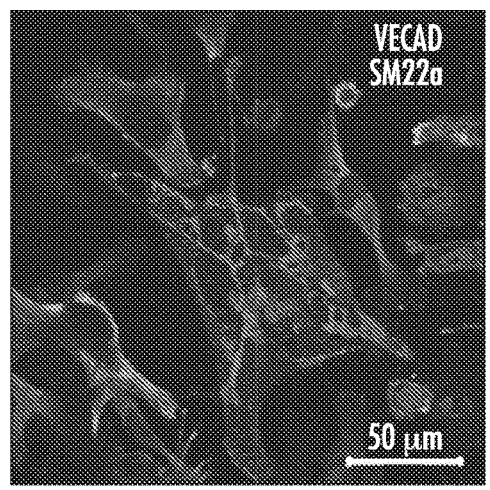
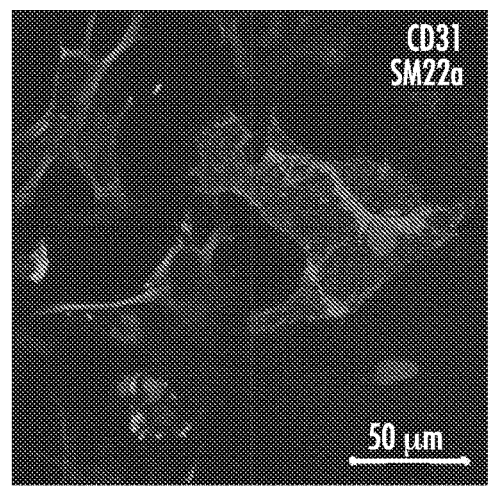
FIG. 10D  FIG. 10E

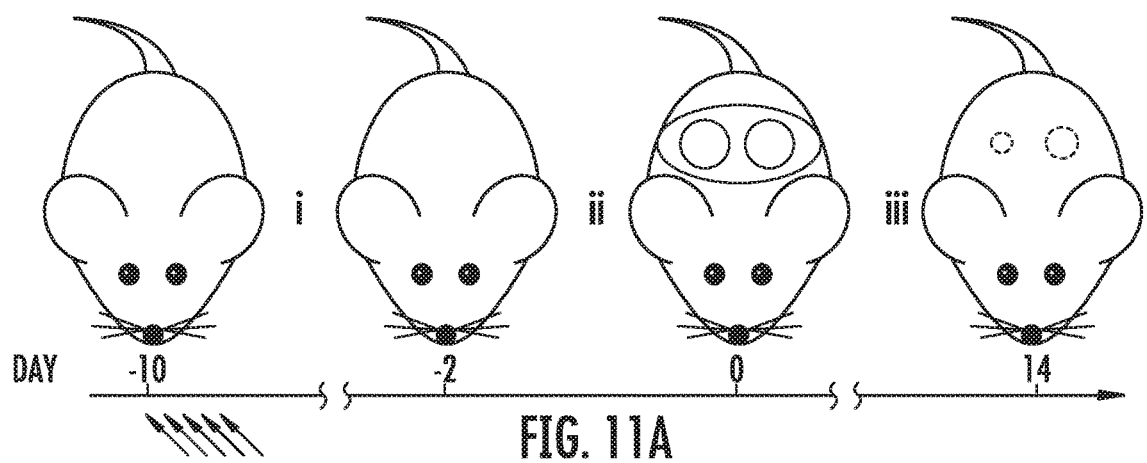
FIG. 11A
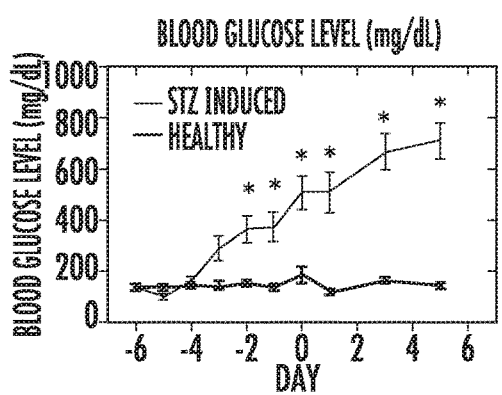
FIG. 11B
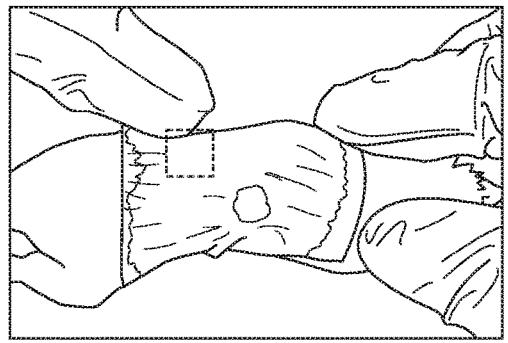
FIG. 11Gi
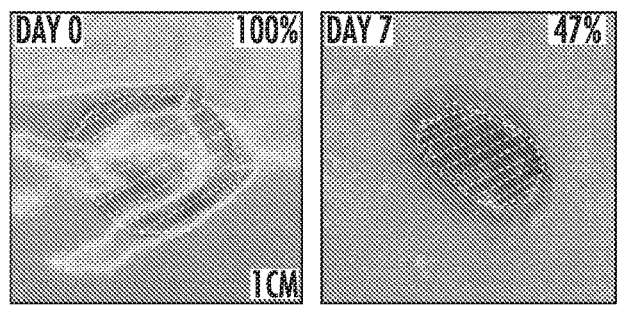
FIG. 11Gii

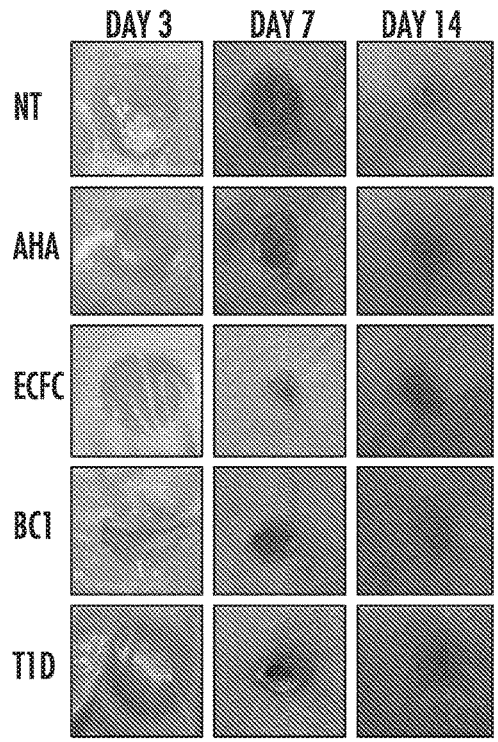
FIG. 13A
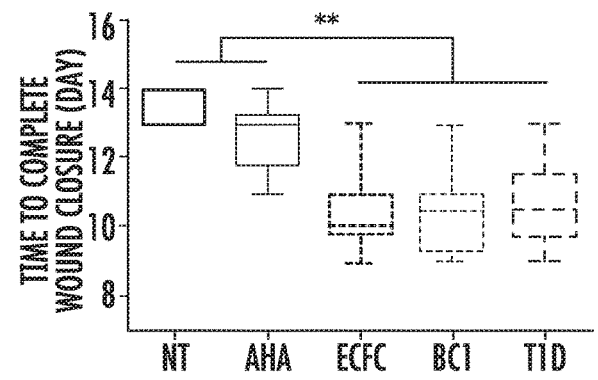
FIG. 13B
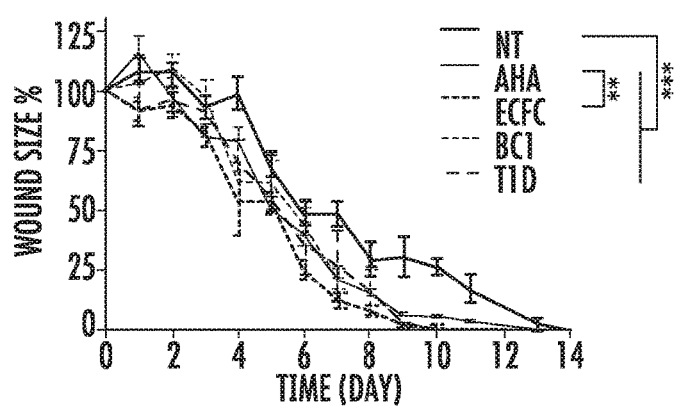
FIG. 13C
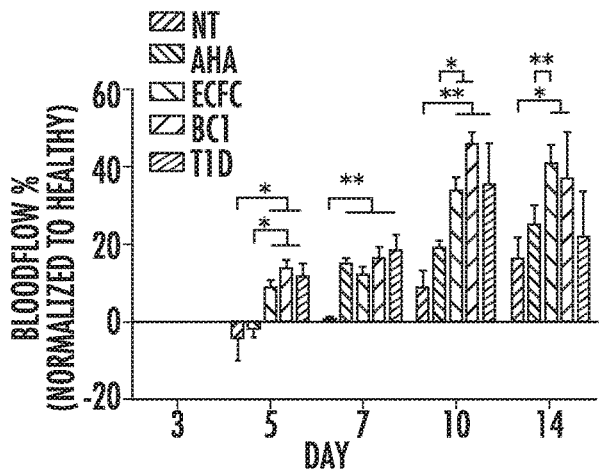
FIG. 13Di
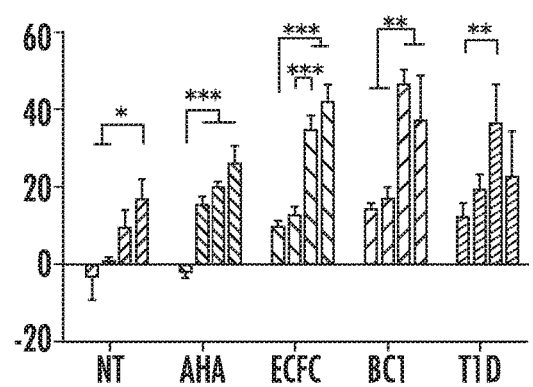
FIG. 13Dii

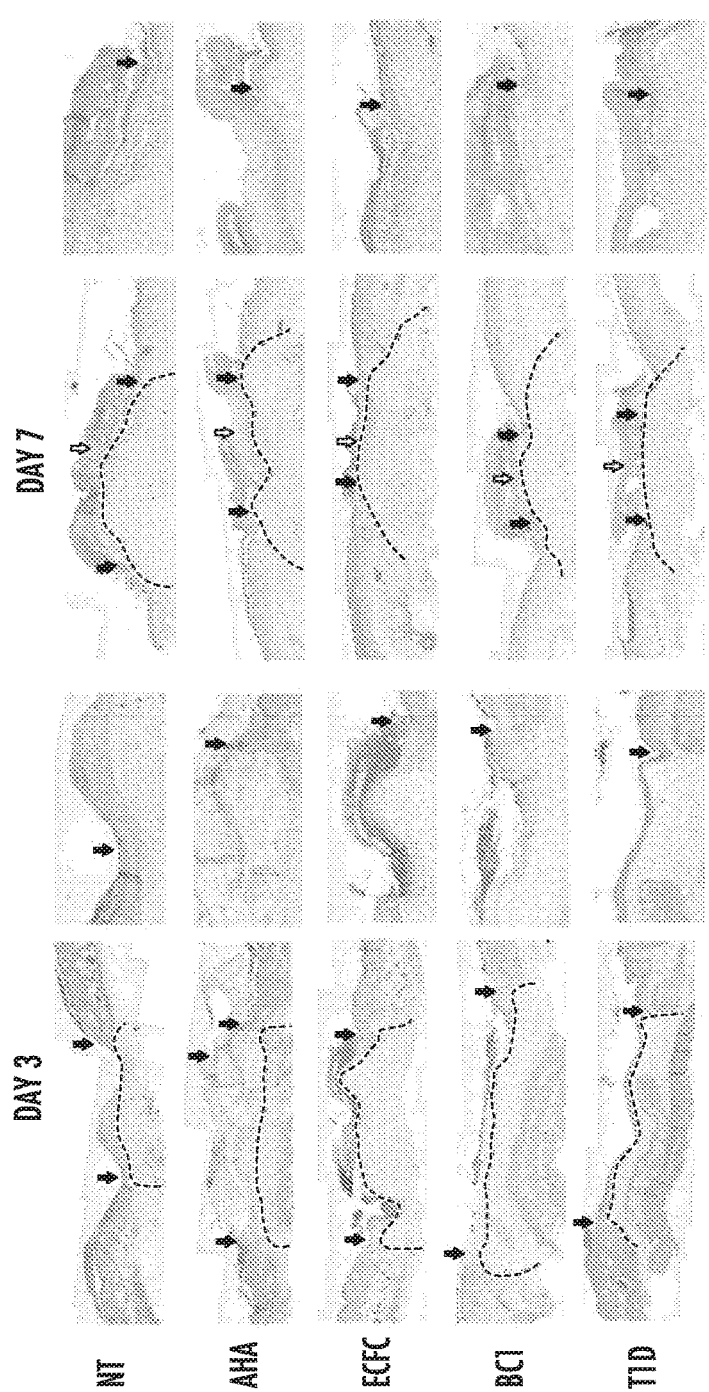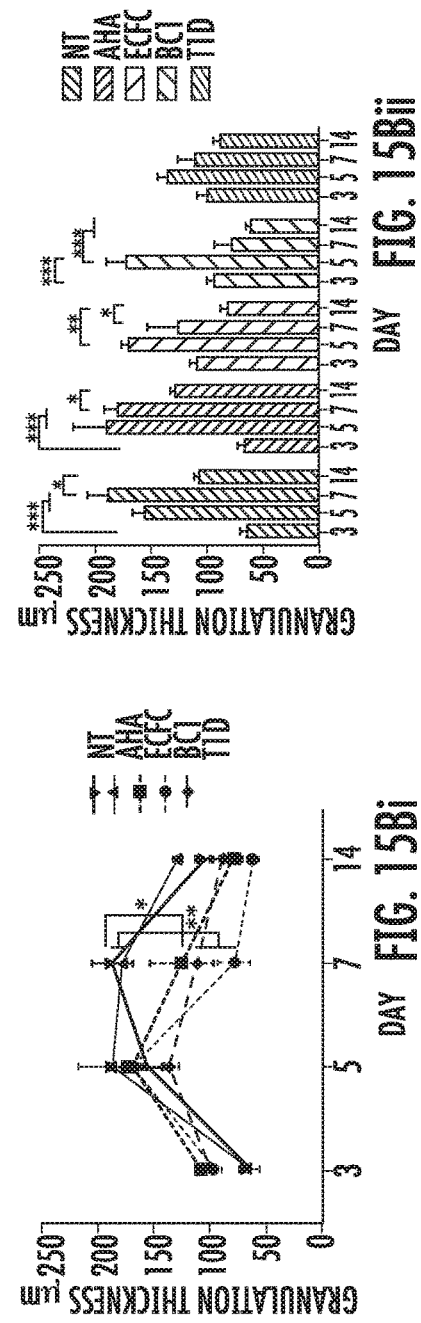
FIG. 15A
FIG. 15Bi
FIG. 15Bii

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Cys Gly Tyr Gly Arg Gly Asp Ser Pro Gly
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Cys Arg Asp Gly Pro Gln Gly Trp Gly Gln Asp Arg Cys Gly
1               5                   10                  15

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Gly Asp Ser
1
```

THREE-DIMENSIONAL VASCULAR NETWORK ASSEMBLY FROM INDUCED PLURIPOTENT STEM CELLS

CROSS-REFERENCE TO RELATED APPLICATIONS

This application is a 35 U.S.C. § 371 U.S. national entry of International Application PCT/US2016/043231, having an international filing date of Jul. 21, 2016, which claims the benefit of U.S. Provisional Application No. 62/195,644, filed Jul. 22, 2015, the content of each of the aforementioned applications is herein incorporated by reference in their entirety.

STATEMENT OF GOVERNMENTAL INTEREST

This invention was made with government support under grant no. R01HL107938 awarded by the National Institutes of Health. The government has certain rights in the invention

SEQUENCE LISTING

The instant application contains a Sequence Listing which has been submitted electronically in ASCII format and is hereby incorporated by reference in its entirety. Said ASCII copy, created on Oct. 29, 2021, is named 02240_538630_SL.txt and is 1,074 bytes in size.

BACKGROUND OF THE INVENTION

Cardiovascular diseases (CVD) are currently a leading cause of death in the United States. Studies have demonstrated that due to hyperglycemia, diabetes patients have a higher risk of developing CVD. Under prolonged hyperglycemic conditions, physiological changes in diabetic patients cause aberrant angiogenesis in both micro and macro vasculatures, which result in CVD such as coronary heart disease and peripheral arterial disease. High blood glucose also impairs endothelial progenitor cell (EPC) functionality and causes poor neovascularization in response to hypoxia, directly affecting wound healing process in diabetic patients. Thus, generation of regenerative vasculatures holds strong promise in treating diabetic patients with CVD and wound healing complications. Stem cells, defined by their ability to self-renew and differentiate into multiple mature cell types are emerging as a promising source for non-invasive approach of tissue regeneration including vascular regeneration. Autologous vascular stem cell therapy could contribute as a potential source for ECs to treat CVD. One such example would be the endogenous EPCs. EPCs can be isolated, expanded in vitro and transplanted to improve revascularization in ischemic cardiovascular diseases. Theoretically, EPCs represent a great candidate for vascular therapy. Unfortunately, the functions of EPCs are compromised under high glucose conditions in diabetes. An alternate source of stem cells for vascular therapy is human induced pluripotent stem cells (hiPSCs). The discovery of the hiPSCs makes stem cell therapy particularly attractive, for example in individuals with diabetes. Reprogrammed hiPSCs offer not only an autologous therapy approach but also the potential of reversing the stress effects of high glucose caused by diabetes. Thus, hiPSCs may provide a renewable cell source for diabetic patients that could improve wound-healing outcomes; this represents an unmet need in the art that has not been addressed or solved in the manner described by embodiments of the instant invention.

SUMMARY OF THE INVENTION

Previous methods have established a step-wise differentiation scheme to generate a bicellular population of early vascular cells (EVCs) consisting of VEcad-positive (VEcad+) cells (early ECs) and PDGFRβ-positive (PDGFRβ+) cells (early pericytes) from a healthy hiPSC line. The EVCs can be further matured to ECs or pericytes. When encapsulated in a synthetic hyaluronic acid (HA) hydrogel, EVCs self-assemble to form functional three-dimensional (3D) vascular networks. However, such methods did not determine if EVCs can be derived from Type 1 diabetes patient-derived hiPSCs. Embodiments of the instant invention include methods of deriving EVCs from Type I diabetes (T1D) patient-derived hiPSCs. These EVCs can mature into functional ECs and assemble into vascular networks in synthetic hydrogel as a response to hypoxic surroundings. Embodiments of the instant invention, include differentiation of T1D hiPSC to EVCs, increasing the portion VEcad+ cells in the EVCs and enhancing the ability of T1D EVCs to mature to functional ECs. In embodiments of the invention, the ability of T1D EVCs encapsulated in a synthetic HA hydrogel to undergo morphogenesis and self-organize to form 3D vascular networks was evaluated. Other embodiments of the invention improve the ability of T1D EVCs to undergo morphogenesis to form 3D vascular networks in response to hypoxic conditions, as is demonstrated using a hypoxia inducing (HI) hydrogel. The current invention provides methods to differentiate T1D-hiPSCs into EVCs, maturation into functional ECs, and generation of vascular networks in a deliverable hydrogel and as a response to hypoxia. Overall, this approach provides us a unique opportunity to advance autologous therapy for diabetic-vascular complications, especially diabetic wound healing, for example diabetic foot ulcers.

In diabetics, hyperglycemia results in deficient endothelial progenitors and cells, leading to cardiovascular complications. An embodiment of the invention is engineered three-dimensional (3D) vascular networks in synthetic hydrogels from type-1 diabetes (T1D) patient-derived human induced pluripotent stem cells (hiPSCs). Such an embodiment can serve as a transformative autologous vascular therapy for diabetic patients. An embodiment of the invention is a feeder free differentiation method to derive early vascular cells (EVCs) with high portion of VEcad+ cells from hiPSCs. The method provides similar differentiation efficiency from hiPSCs derived from healthy donor and T1D patient. T1D-hiPSC derived VEcad+ cells can mature to functional endothelial cells (ECs) expressing mature markers such as CD31 and von Willebrand factor (vWF), are capable of lectin binding and acetylated low-density lipoprotein (acLDL) uptake, form cords on Matrigel and respond to tumor necrosis factor alpha. When embedded in engineered hyaluronic acid (HA) hydrogels, T1D-hiPSC derived EVCs (T1D-EVCs) undergo morphogenesis and assemble into 3D networks. When encapsulated in a HI hydrogel, T1D-EVCs respond to low oxygen and form 3D networks, a result that has previously never been realized.

Embodiments of the invention include a robust differentiation protocol in which T1D-hiPSC can be directed to efficiently differentiate into EVCs. Early ECs derived from T1D-hiPSC are fully functional when mature. T1D-EVCs self-assemble into 3D network while embedded in both HA and HI hydrogels. The capability of T1D-EVCs to assemble into 3D networks in engineered matrices and respond to a hypoxic microenvironment is a significant development for autologous vascular therapy in diabetic patients and has broad importance for tissue engineering.

An embodiment of the present disclosure includes a method for differentiating human-induced Pluripotent Stem Cells (hiPSCs) into Early Vascular Cells (EVCs) in vitro. The method includes the steps of: plating a single-cell suspension of hiPSCs onto a suitable surface; adding culture medium; adding a Rho associated coiled coil containing kinases (ROCKs) inhibitor to the culture medium; culturing the cells; and harvesting the resulting EVCs. In other embodiments, differentiated EVCs are encapsulated in a hydrogel following harvesting. In embodiments, the hiPSCs are type-1 diabetes (T1D) patient-derived hiPSCs human induced pluripotent stem cells. In any embodiment, the ROCKs inhibitor can be Y27632. In embodiments, the single-cell suspension of hiPSCs has a cell seeding density of between 5×10$^4$ cells/cm2 and 1×10$^5$ cells/cm2. The EVCs can include cells that express vascular endothelial cadherin (VEcad+ cells) and/or cells that express platelet derived growth factor β (PDGFβ+ cells). In some embodiments, at least 47% of the EVCs are VEcad+ cells. Embodiments of the method can also include the step of encapsulating the EVCs in a hydrogel following the step of harvesting, for example an oxygen-controllable and hypoxia-inducible hydrogel. In embodiments utilizing a hydrogel, the hydrogel can be a hyaluronic acid (HA) hydrogel or a collagen hydrogel. A second embodiment of the present disclosure includes a cell population of EVCs differentiated in vitro from hiPSCs. The EVCs can include cells expressing vascular endothelial cadherin (VEcad+ cells) and cells expressing platelet derived growth factor receptor β (PDGFRβ+ cells). The EVCs can be differentiated in vitro from hiPSCs according to the methods described herein.

Another embodiment of the present disclosure includes a method of generating a vascular network by the steps of providing Early Vascular Cells (EVCs) derived from human-induced Pluripotent Stem Cells (hiPSCs); and encapsulating the EVCs in a hydrogel. According to this embodiment, the hiPSCs can be type-1 diabetes (T1D) patient-derived human induced pluripotent stem cells. The EVCs are differentiated according to methods described herein. The hydrogel can be, for example, a hyaluronic acid (HA) hydrogel or a collagen hydrogel, and can be an oxygen-controllable hydrogel or a hypoxia-inducible hydrogel.

An embodiment of the present invention includes a method for differentiating hiPSCs into EVCs in vitro, comprising the steps of: plating a single-cell suspension of hiPSCs onto a suitable surface; adding serum free culture medium; adding a Rho associated coiled coil containing kinases (ROCKs) inhibitor to the medium; culturing the cells; and harvesting the resulting EVCs.

An embodiment of the present invention includes a method for differentiating hiPSCs into EVCs in vitro, comprising the steps of: plating a single-cell suspension of hiPSCs onto a suitable surface; adding a Rho associated coiled coil containing kinases (ROCKs) inhibitor; culturing hiPSCs to 60-80% confluency; replacing with serum free culture medium; adding a GSK3 inhibitor CHIR99021; culturing the cells; and harvesting the resulting EVCs.

Examples of hiPSCs suitable for use in the present invention are those derived from a patient with a vascular disorder, such as diabetes and pulmonary hypertension, derived from a patient with a HIF2 α+ mutation, and/or derived from an UTHIF2a cell line. The EVC produced by the methods of the present invention may form EVC networks comprising cells and pericytes that have undergone vasculogensis, and/or formed functional microvascular networks. EVC networks may be administered to the wound of a subject to enhance healing and may be administered by implantation in to a wound, such as diabetic wound in a diabetic subject, to reestablish blood flow and improve the wound healing rate. The wound healing rate may be determined by comparing wound healing of a wound, such as a diabetic ulcer, that has been administered Early Vascular Cells Networks with the wound healing of a reference wound, such as a reference diabetic ulcer, that has not been administered Early Vascular Cells Networks. The EVCs produced by the methods of the present invention may be encapsulated in a hydrogel, for example, a hyaluronic acid (HA) hydrogel, collagen hydrogel, or a hydrogel comprising a combination thereof. An oxygen-controllable and hypoxia-inducible hydrogel may also be used to encapsulate EVCs of the present invention. A hypoxia-inducible hydrogel may have less than 5% dissolved oxygen, less than 4% dissolved oxygen, less than 3% dissolved oxygen, less than 2% dissolved oxygen, or less than 1% dissolved oxygen. An oxygen gradient hydrogel is formed by controlling the balance of the diffusion of oxygen through the top of the gel and of the consumption of oxygen uptake by the cells. The oxygen gradient formed within the gel is in the range of about 0.1% to 21% of dissolved oxygen content, 1% to 17% dissolved oxygen content, 3% to 15% dissolved oxygen content, or 5% to 10% dissolved oxygen content.

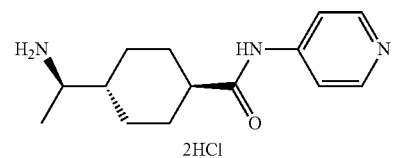

Y-27632 2HCL Chemical Structure

Abbreviations

Certain abbreviations are used throughout the specification for simplicity including: 3-dimensional (3D); acetylated low-density lipoprotein (acLDL); cardiovascular diseases (CVD); endothelial cell (EC); endothelial progenitor cell (EPC); early vascular cell (EVC); human-induced pluripotent stem cell (hiPSC); hyaluronic acid (HA); hypoxia-inducible (HI); platelet-derived growth factor β (PDGFRβ); rho associated coiled coil containing kinase (ROCK); type 1 diabetes (T1D); type 1 diabetes human-induced pluripotent stem cell derived early vascular cell (T1D-EVC); vascular endothelial cadherin (VEcad)

BRIEF DESCRIPTION OF THE DRAWINGS

FIG. 1A-1E shows a method of EVC differentiation.
FIG. 3A-3D shows characterization of EVCs derived from T1D-hiPSCs.
FIG. 4A-4E shows maturation of functional T1D ECs from T1D-EVCs.

FIG. 9A-9B shows individual EVC differentiation of hiPSC lines UT2HIF2α and C12-GFP.

FIG. 10A-10E shows characterization of EVCs derived from T1D-hiPSC 1018S cell line.

FIG. 11A-11C shows a diabetic immunodeficient mouse model. (A) Schematic drawing of the timeline of DFU immunodeficient diabetic mellitus wound model in mice (i) 5 daily consecutive 50 mg/kg STZ injection. (ii) Glucose levels exceeded 300 mg/dL on 2 consecutive readings 47 hours apart was selected. (iii) At day 0, two 6 mm full thickness punch wounds were created. Treated vs non-treated served as control and dressed with Tegaderm. (B) Blood glucose measurements. 300 mg/dL is considered diabetic (C) Photos showing (i) wound after bandage using betadine and tegaderm and (ii) planetary measurement of the wound (shown at day 0 & 7). Shaded area is calculated as wound area (in this example, 100% on day 0 and 47% on day 7). Scale bar is 1 cm.

FIG. 13A-13C shows macroscopic analysis for diabetic wound healing. (A) Closure of wounds treated with acellular (NT, AHA) and cellular (ECFC, BC1, T1D) constructs and wounds receiving no-treatment. Representative planetary photos of wounds at day 3, 7 and 14 (B) Time of full closure of the wounds. C) Wound closure progression along the treatment period. (Di) Blood flow profile of different treatment groups at the same time point and (Dii) bloodflow profile progression over time within each group. Note that here we consolidated all NT controls together from all other control groups because no significant differences were observed among them. Scale bar is 1 cm. n=12 for ECFC, EVC-BC1 and EVC-T1D n=6 for AHA and n=42 for NT.

FIGS. 15A, 15Bi, and 15Bii shows histological sections of wounds during closure. Representative images of H&E stained histological sections of wounds on (A) day 3 and day 7 are shown with the respected treatment groups. Higher magnification is shown right of the overview images. Eschar is labelled with yellow arrows. Red arrows indicate some non-degraded gel. Black arrows indicate leading wound edge. White dash line outline the granulation layer during healing. (Bi, Bii) Quantification of granulation layer thickness in comparison between groups at the same time point (Bi) and progression over time with specific treatment (Bii). N=3 each. Scale bar is 500 μm.

DETAILED DESCRIPTION OF THE INVENTION

Figure 2B:
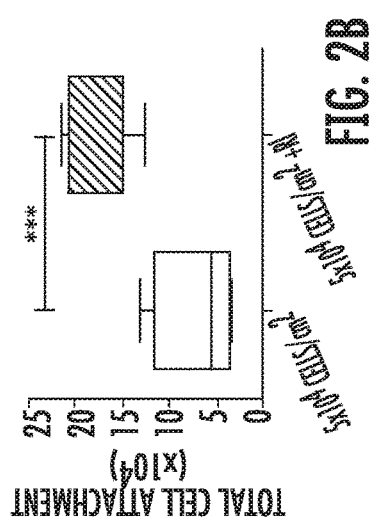
FIG. 2A-2D shows EVC Differentiation of T1D-hiPSCs.

Previous methods involving a two-step, adherent culture protocol for the controlled differentiation of hESCs and healthy hiPSCs into a bi-cellular EVC population have been described. These methods do not describe how to generate the specific population of EVCs described in embodiments of the instant invention. During the first six days of the differentiation scheme, seeded single-cell hiPSCs were induced to become mesodermal. Upon reseeding on day 6, they proceed to differentiate into EVCs for another six days (FIG. 1A). This EVC population consists of VEcad+ early ECs and PDGFRβ+ early pericytes. Certain embodiments of the invention can provide a therapeutic solution for diabetic-vascular complications. As such, the present invention provides a method to induce EVC differentiation from T1D-hiPSCs and increase EC yield in the EVC population, because a higher EC yield more closely mimics the in vivo EC to pericyte ratio in the average microvessels.

A healthy individual-derived BC1-hiPSC line (a completely sequenced hiPSC cell line derived from bone marrow CD34+ cells via non-viral reprogramming techniques) was used. In previous methods, the addition of Rho associated coiled coil containing kinases (ROCKs) inhibitor Y27632 has been shown to improve the survival of the single hiPSC. Also, previous methods have shown that the initial cell seeding density can affect the differentiation efficiency of the pancreatic endocrine cells. However, these methods have not been shown to be useful in deriving the population of EVCs as described in certain embodiments of the instant invention. More specifically, previous methods have failed to show or suggest that Y27632 can be used in a differentiation protocol to differentiate stem cells into endothelial cells or EVCs. According to embodiments of the invention, adding Y27632 significantly increases endothelial cell populations following differentiation. Accordingly, in embodiments of the invention, differentiation media is supplemented with Y27632 and the initial cell seeding was increased from $5 \times 10^4$ cells/cm$^2$ to $1 \times 10^5$ cells/cm$^2$. By comparing total EC yield from previously reported data and the methods of current invention, (FIG. 1A), it was observed that when seeding at a higher density, $1 \times 10^5$ cells/cm$^2$, an overall increase in total cell attachment resulted, in comparison to the control, previous protocol seeded at $5 \times 10^4$ cells/cm² (FIG. 1Bi-ii); this was an unexpected result. When ROCK inhibitor was added to cultures seeded at 5×10⁴ cells/cm², most seeded cells were attached to the plate at around 50-60% confluency (FIG. 1Biii). In contrast to cells in culture using the original protocol and protocol with increasing cell seeding density only, the ROCK supplemented cells appeared more compact and less spindle-like, adapting a cobble stone-like morphology (FIG. 1Biii). Also, it was found that addition of ROCK inhibitor on day 0 increased the cell survival and cell attachment of BC1 hiPSC after 24-hour period, resulting in an at least 3-fold difference in the total number of cells attached between control and ROCK suppressed cultures (FIG. 1C). By increasing cell-seeding density from 5×10⁴ cells/cm² to 1×10⁵ cells/cm² on day 0, there was a 2-fold increase in total cell attachment after 24 hours (FIG. 1C). On day 12 of differentiation, cells in culture using the original protocol (control) are not confluent and they appeared mostly elongated and spindle-like (FIG. 1Di). On the contrary, cells in culture either seeded at a higher density or using ROCK inhibitor both appeared as patches of cobblestone-like cells surrounded by cells that are spindle-like and elongated (FIGS. 1Dii and 1Diii). Importantly, an increased total yield of VEcad+ cells in the modified differentiation methods was observed. The total yield of VEcad+ cells for ROCK inhibitor supplemented differentiation is 41.76±17.05% (n=3) and for high initial cell seeding density is 62.0.0±14.9% (n=6) compared to our original protocol, which yielded 18.9±14.9% VEcad+ cells (n=4; FIG. 1E).

FIG. 1 shows a method of EVC differentiation. (A) Schematics of the differentiation procedure time line and the modified protocols examined. (B) Light microscopy (LM) images of the differentiating EVCs on day 1 in three different conditions examined. (i) Control: 5×10⁴ cells/cm²—have low cell attachment and spindle-like morphology (some indicated by black arrowheads); (ii) 1×10⁵ cells/cm²—have higher cell attachment and some spindle-like morphology (some indicated by black arrowheads); (iii) 5×10⁴ cells/cm² and ROCK inhibitor supplement—have highest cell attachment and universally more relaxed, cobble stone-like morphology. (C) Quantification of cells attachment after 24 hours in the three conditions examined. (D) LM images of the differentiating EVCs on day 12 in the three different conditions examined. (i) Control: 5×10⁴ cells/cm²—have elongated, spindle-like morphology; (ii) 1×10⁵ cells/cm² and (iii) 5×10⁴ cells/cm² and ROCK inhibitor supplement—both have cells with cobble stone-like morphology (white open arrowheads) surrounded by spindle-like cells. (E) Representative flow cytometry analysis of VEcad and PDGFRβ expression in BC1 EVCs derived in the three conditions. Scale bars are 100 μm. Significance levels were set at *p<0.05, p<0.01, and *p<0.001.

EVC Differentiation from T1D Patient-Derived hiPSC.

Figure 2D:
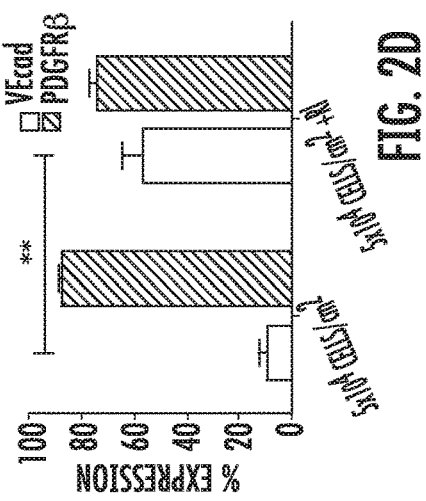
Figure 2A:
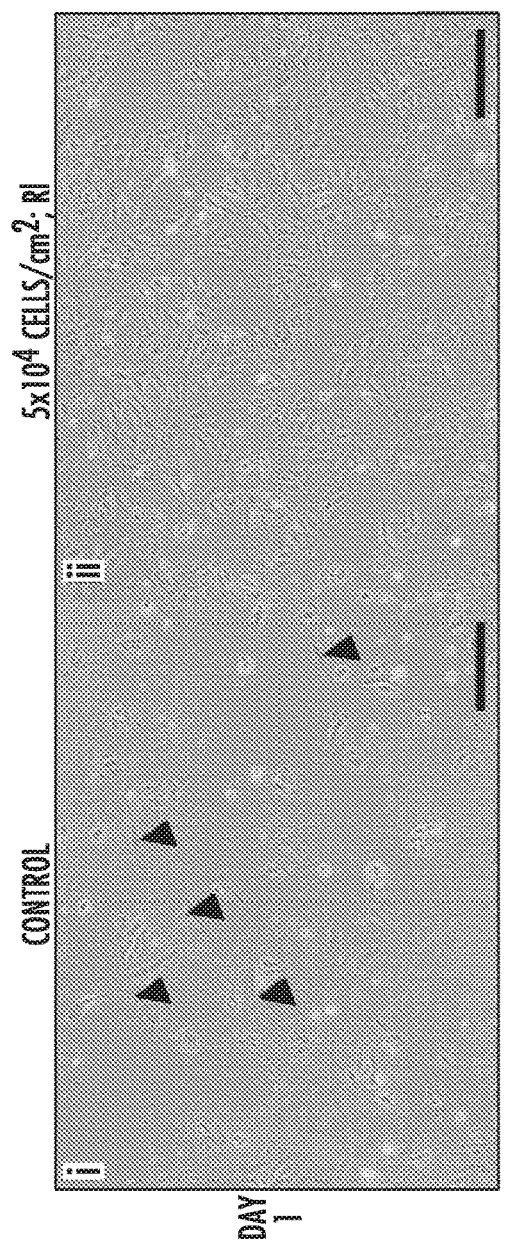
Figure 2C:
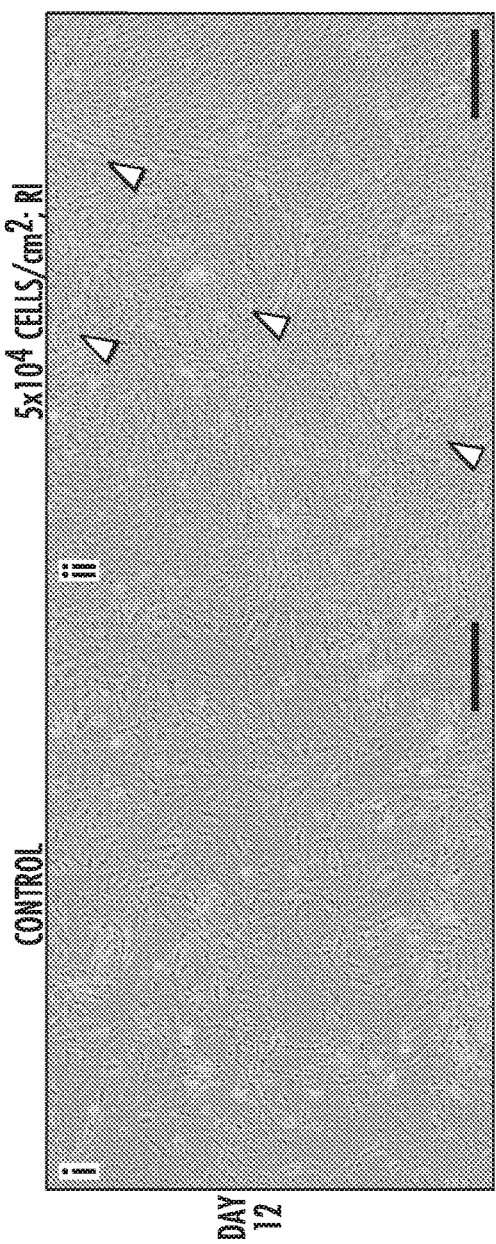

According to the invention, hiPSCs derived from patients with vascular complications have similar differentiation potential to BC1 hiPSC derived from a healthy donor. To demonstrate this property, a T1D patient-derived hiPSC line, H2.1, was utilized to generate a bi-cellular population of EVCs. A prior differentiation protocol and the improved differentiation protocol of the present invention were compared, with focus on supplementation of ROCK inhibitor. Similar to BC1, on day 1, in comparison to the culture without ROCK inhibitor addition (FIG. 2Ai), the ROCK inhibitor supplemented cells attached better and had a morphology that is more relaxed and less spindle-like (FIG. 2Aii). The addition of ROCK inhibitor on the initial day (day 0) to the T1D-hiPSC resulted in at least 2-fold increase of the total attached cells (FIG. 2B). On day 12 of the differentiation, when compared to cells cultured using the original protocol, which most of the cells appeared to be spindle-like and elongated (FIG. 2Ci), the cells cultured using ROCK inhibitor appeared to be cobblestone-like in groups, suggestive of an endothelial-like morphology (FIG. 2Cii). By supplementing ROCK inhibitor in T1D-hiPSC differentiation experiments, the same effect of generating high yield of VEcad+ cells was observed. Altogether, the effect of ROCK inhibition is similar in the T1D-hiPCs to the case of the BC1 hiPSC. Accordingly, it was found that altering the differentiation protocol tremendously and unexpectedly improved the total number of resulting early ECs (FIG. 2D). At the end of the EVC differentiation step (day 12), a cell population with 48.5±19.7% VEcad+ cells and 73.21±11.25% PDGFRβ+ cells (FIG. 3A) was generated. Moreover, in the method of differentiation VEcad+ cells that are also positive for CD31, a mature endothelial cell marker at 43.0±15.0% (FIG. 3B) were observed. Similar to the BC1 hiPSC-derived EVCs, a small subset of T1D-derived VEcad+ cells also express PDGFRβ (FIG. 3C). Immunofluorescence staining showed that the T1D hiPSC-derived EVCs (T1D-EVCs) contain early ECs with the typical cobblestone morphology, with both VEcad and CD31 localized to the intercellular junctions as well as elongated PDGFRβ+ cells (FIGS. 3D and 3E).

FIG. 2 shows EVC Differentiation of T1D-hiPSCs. (A) LM images of the differentiating EVCs on day 1 in two different conditions. (i) Control: 5×10⁴ cells/cm² and (ii) 5×10⁴ cells/cm² and ROCK inhibitor supplement. White arrowheads indicate cobble stone-like morphology. (B) Quantification of cells attachment after 24 hours in the two conditions examined. (C) LM images of the differentiating EVCs on day 1 in two different conditions. (i) Control: 5×10⁴ cells/cm² and (ii) 5×10⁴ cells/cm² and ROCK inhibitor supplement. (D) Representative flow cytometry histogram of VEcad and PDGFRβ expression in T1D-EVCs derived in the two conditions. Scale bars are 100 μm. Significance levels were set at *p<0.05, p<0.01, and *p<0.001.

FIG. 3 shows characterization of EVCs derived from T1D-hiPSCs. (A) Flow cytometry histogram showing expression of VEcad, CD31 and PDGFRβ in T1D-hiPSC derived EVCs. (B) Representative flow cytometry dot plot showing overlapping of VEcad and CD31-positive cells. (C) Representative flow cytometry dot plot showing overlapping of PDGFRβ+ and VEcad+ cells. Immunofluorescence (IF) images of EVCs stained for (D) VEcad (in red) and PDGFRβ (in green); nuclei (in blue), and (E) CD31 (in red) and PDGFRβ (in green); nuclei (in blue). Scale bars are 100 μm.

EC Maturation of T1D-EVCs.

The endothelial maturation and functionality potential from T1D-EVCs was examined next. The VEcad+ cells were sorted and expanded under the same differentiation culture conditions. VEcad+ cells were sorted using magnetic sorting and more than 90% VEcad expression of the sorted cells was confirmed using flow cytometry (FIG. 4A). Sorted VEcad+ cells were subcultured and expanded for another 6 days, in which they maintained the cobblestone morphology of typical ECs (FIG. 4B), compared to VEcad-cells where most cells appeared fibroblast-like (FIG. 4B). These ECs exhibited typical membrane expression of VE-cad and CD31, cytoplasmic punctuate expression of von Willebrand factor (vWF). These cells also demonstrated the ability to bind to lectin *Ulex europaeus* and uptake of acetylated low density lipoprotein (acLDL; FIG. 4C). These ECs formed cord when seeded on top of Matrigel (FIG. 4D). In addition, T1D-hiPSC-differentiated ECs respond to inflammatory cytokine, tumor necrosis factor alpha (TNFα) by upregulated expression of intercellular adhesion molecule 1 (ICAM-1; FIG. 4E). Overall, T1D hiPSC-differentiated ECs (T1D-ECs) exhibit mature endothelial characteristics consistent with ECs derived from healthy BC1-hiPSC control.

FIG. 4 shows maturation of functional T1D-ECs from T1D-EVCs. (A) Representative flow cytometry histogram for VEcad expression of magnetic sorted VEcad+ cells. (B) LM images of sorted VEcad+ and VEcad− cells that were subcultured for an additional 6 days. (C) IF images of sorted and subcultured VEcad+ cells for: VEcad, CD31, vWF, eNOS, binding of *Ulex europaeus* fluorescein-conjugated lectin, and uptake of acLDL. Marker in red or green as indicated on each figure panel; nuclei in blue. (D) LM image of T1D-ECs forming cord on Matrigel. (E) T1D-ECs responded to TNFα via upregulation of ICAM-1 expression assessed using flow cytometry. Significance levels were set at *$p<0.05$, $p<0.01$, and *$p<0.001$.

The differentiation protocols described above were also applied to three additional hiPSC lines: UTHIF2α, C12-GFP and 1018S. UTHIF2α is a hiPSC line provided by Dr. Linzhao Cheng and is derived using the same methods used for the derivation of BC1 hiPSC. The cells are derived from a patient with HIF2 α+ mutation. C12-GFP is a healthy hiPSC transduced with GFP previously described.[54] 1018S is a previously characterized and isolated T1D-hiPSC line.

Results for the differentiation of UTHIF2α, C12-GFP and 1018S cells can be seen in FIG. 9 and FIG. 10. More specifically, FIG. 9A shows individual EVC differentiation of UT2HIF2α cells. FIG. 9Bi and Bii shows individual EVC differentiation of C12-GFP cells. FIG. 10 shows the characterization of EVCs derived from 1018S cells. More specifically, panel A shows LM images of the differentiating EVCs on day 1 (i) and day 12 (ii) at $5\times10^4$ cells/cm$^2$ and ROCK inhibitor supplement. White arrowheads indicate cobble-stone like morphology. Scale bars are 100 μm. Panel B shows representative flow cytometry analysis of VEcad and PDGFRβ expression in T1D EVCs. Panel C shows a flow cytometry histogram showing expression of VEcad, CD31 and PDGFRβ in T1D hiPSC derived EVCs. Immunofluorescence (IF) images of EVCs stained for (panel D) VEcad (in red) and SM22a (in green); nuclei (in blue), and (panel E) CD31 (in red) and SM22a (in green); nuclei (in blue) are also shown. Scale bars are 50 μm.

Vascular Assembly of T1D-EVCs in HA Hydrogels.

Figure 5A:
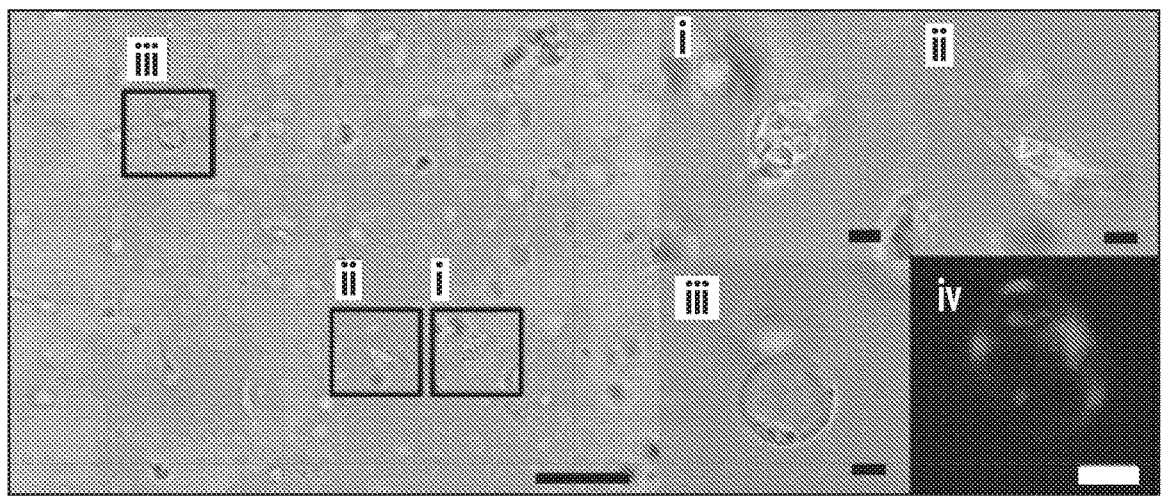
FIG. 5A-5D shows vascular assembly from T1D-EVC in HA hydrogels.
Figure 5B:
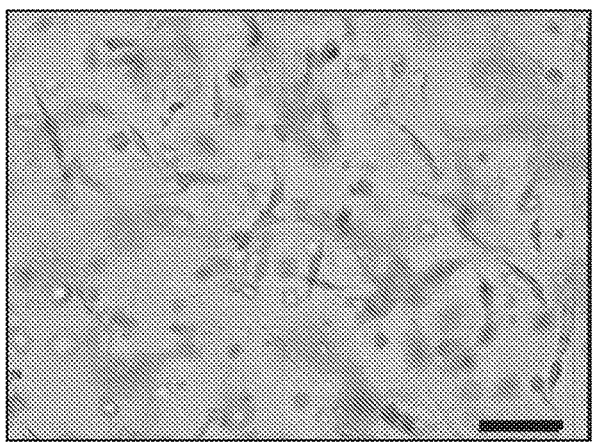
Figure 5C:
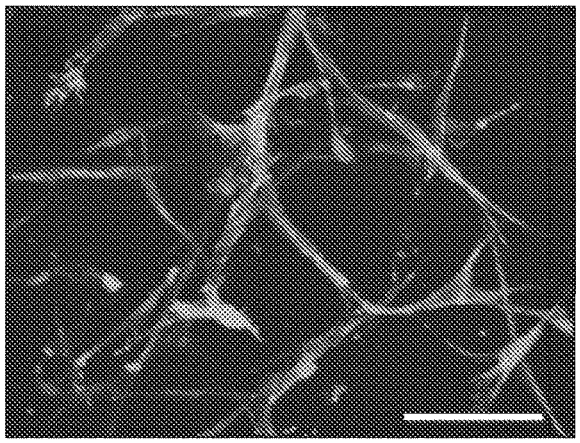
Figure 5D:
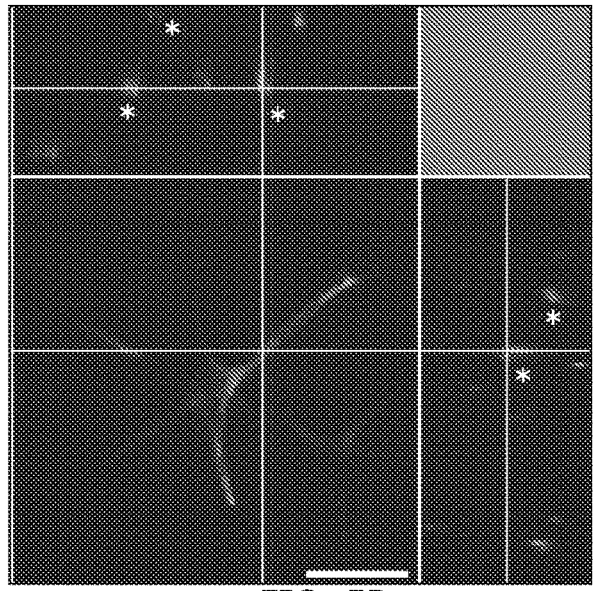

The potential of T1D-EVCs to self-assembly into a microvascular bed was then assessed by examining network formation in synthetic HA-based hydrogel. These engineered HA hydrogels are described in U.S. application Ser. No. 13/844,313, filed Mar. 15, 2013 (Published as US Patent Application Publication No. 2014-0273220A1) and U.S. Application No. 61/846,369, filed Jul. 15, 2013, the entire contents of which are hereby incorporated by reference herein, present adhesion and degradation motives, allowing sequential progression in vascular morphogenesis. The process of T1D-EVC network formation was tracked every day for a total of 3 days. During the first two days after encapsulation of T1D-EVCs in the HA-based hydrogel, vacuole formation was observed in many of the cells, presumably the early ECs (FIG. 5Ai). In some cases, larger lumen formed when multiple vacuoles merged and coalesced into a larger structure (FIG. 5Aiii-iv). Within the same time frame, tubulogenesis, in which many of the cells sprouted (FIG. 5Aii) was also observed. On day 3, an extensive, multicellular network was observed within the hydrogel, which appears to be a complex vascular network (FIG. 5B-C). Lumens were detected within the 3D vascular network (FIG. 5D). By tracking the progression of 3D network formation of encapsulated T1D-EVCs, cellular behavior and network progression that resembles typical vascular morphogenesis was observed. Overall, it was demonstrated that T1D-EVCs are able to self-assemble into a vascular network in a synthetic hydrogel.

FIG. 5 shows vascular assembly from T1D-EVC in HA hydrogels. (A) Within 48 hours of encapsulation, cells have vacuolated and coalesced (i) and sprouted (ii) as visualized using LM images. (iii-iv) Lumen formation was visualized using LM and vacuole stain. Red: FM 4-64 FX; Blue: nuclei. Scale bar for A is 100 μm. Scale bar for each inset is 10 μm. (B) LM image 3 days after EVCs encapsulation in HA showing that microvascular network has begun to form. (C) Confocal image of day 3 microvascular network. Phalloidin (green) and nuclei (blue). (D) Confocal image showing orthogonal view of luminal networks (indicated with asterisks). Scale bars are 100 μm.

Three-Dimensional T1D-EVC Network Formation in HI Hydrogel.

Figure 6A:
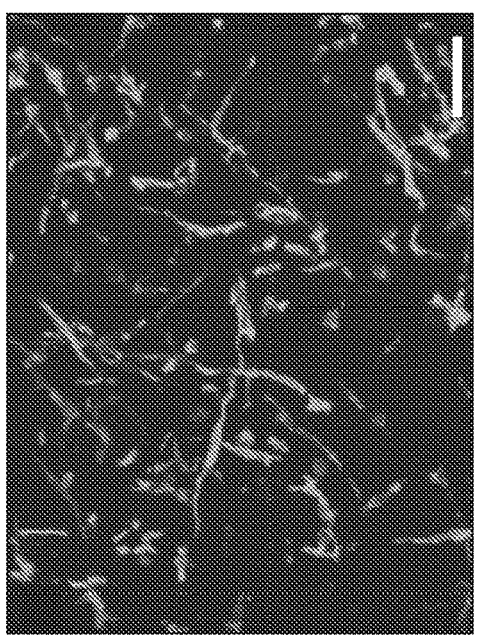
FIG. 6A-6F shows vascular assembly from T1D-EVCs in hypoxic hydrogel.
Figure 6B:
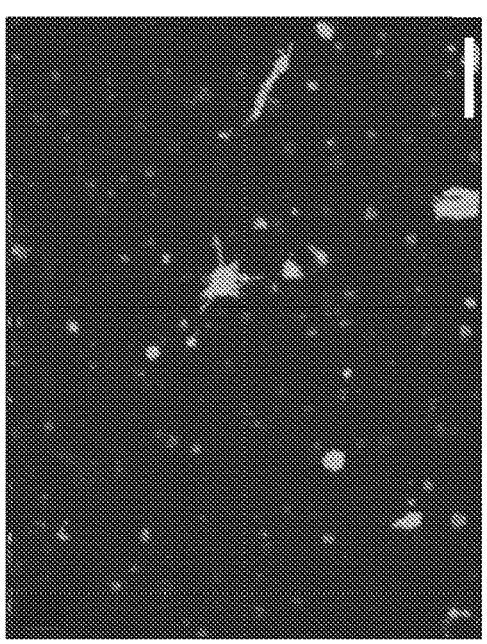
Figure 6C:
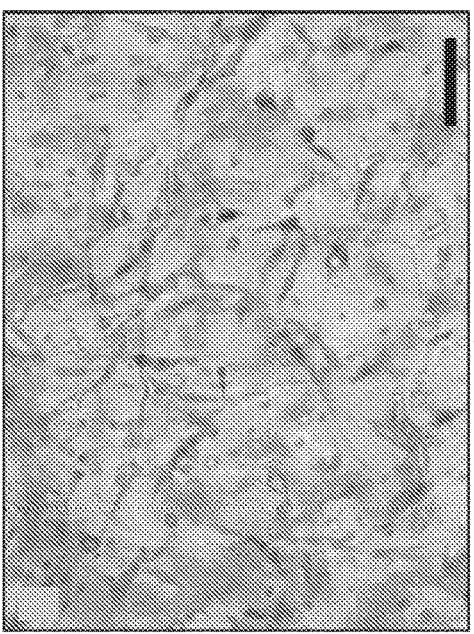
Figure 6D:
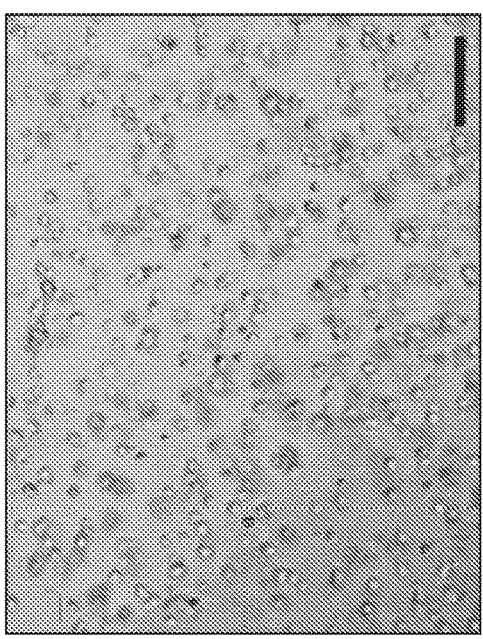
Figure 6E:
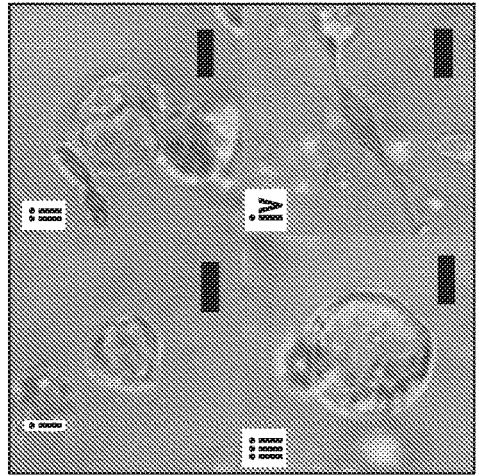
Figure 6F:
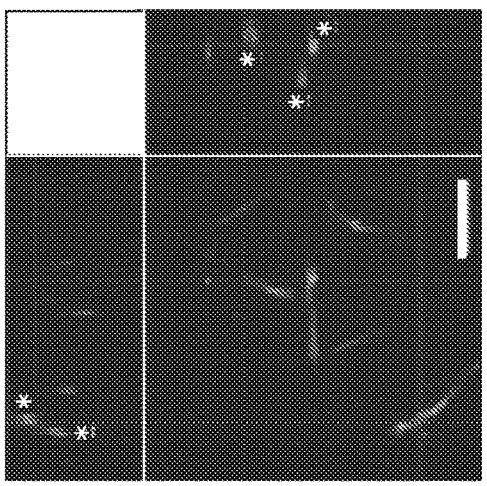
Figure 8A:
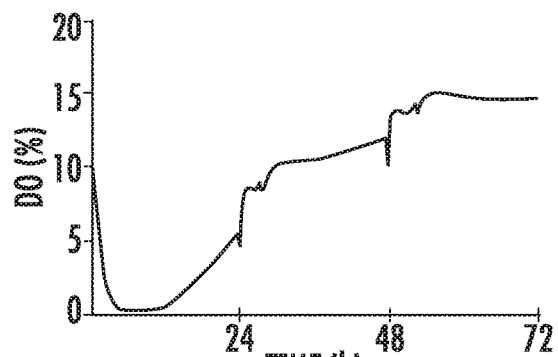
FIG. 8A-8F shows encapsulated T1D-EVCs in hypoxic hydrogel and non-hypoxic hydrogel.
Figure 8B:
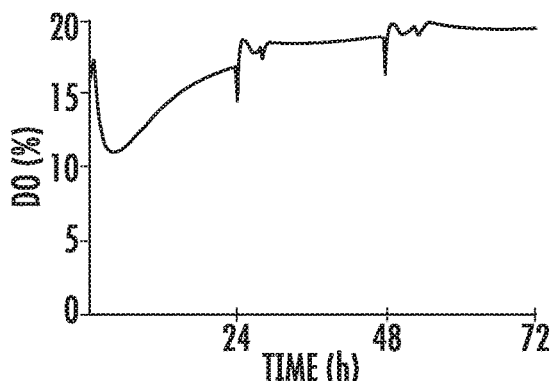
Figure 8C:
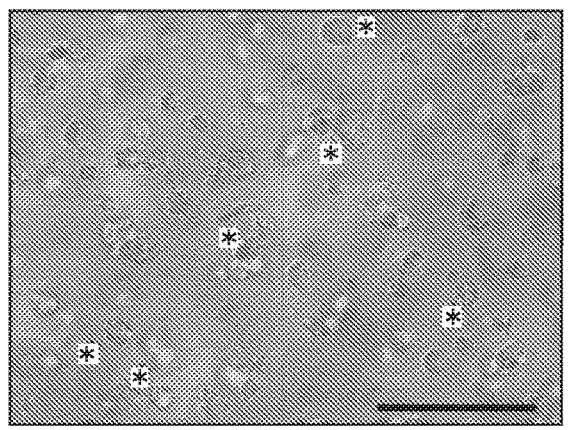
Figure 8D:
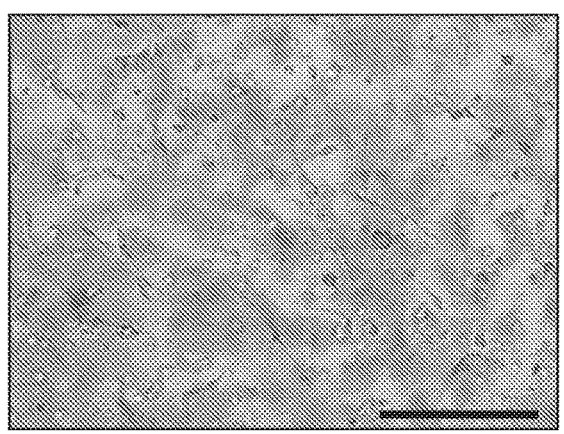
Figure 8E:
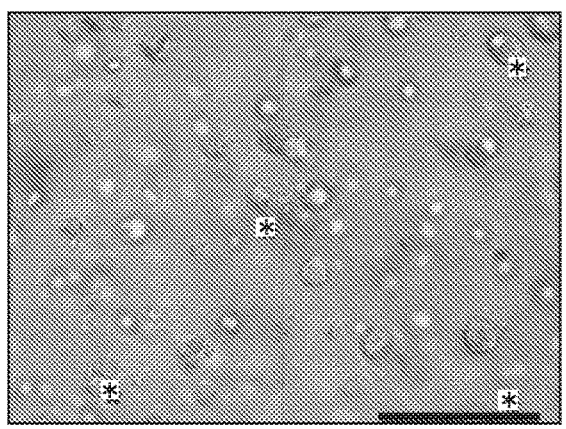
Figure 8F:
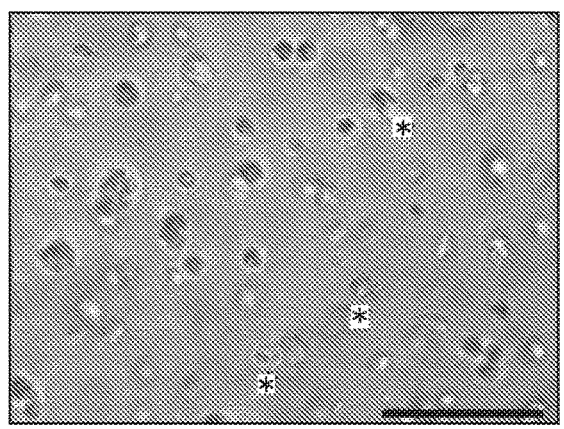

Since EPC-mediated blood vessel formation in diabetic patients is deficient in response to hypoxia, it was determined if T1D-EVCs retain the similar deficits. A novel HI hydrogel system as described in U.S. application Ser. No. 14/536,392, filed Nov. 7, 2014, the entire contents of which are hereby incorporated by reference herein, was employed to encapsulate T1D-EVCs and examine their responsiveness to a hypoxic microenvironment, similar to those of diabetic wounds. T1DEVCs were encapsulated in either non-hypoxic or hypoxic hydrogel (see Materials and Methods), and the process of morphogenesis and network formation was tracked at every 24 hours for a total of 3 days. During the encapsulation period, the dissolved oxygen (DO) level of T1D-EVCs encapsulated in the hypoxic and non-hypoxic hydrogel was recorded to be at a range of 0.1 to 5.0% and 10 to 15%, respectively for the first 24 hours (FIG. 8A). T1DEVCs responded differently within the non-hypoxic and hypoxic hydrogel. In hypoxic hydrogel, T1D-EVCs progressed through all stages of vascular morphogenesis, starting from the formation of individual vacuoles that coalesce to form lumens within the first day (FIG. 6Ai-iii and FIG. 8C) and begun sprouting within the second day of encapsulation (FIG. 6Aiv and FIG. 8D). On day 3, the encapsulated T1D-EVCs eventually formed extensive 3D networks that are lumenized, indicating complete tube formation (FIG. 6B-D). In comparison, within the first two days of non-hypoxic hydrogel encapsulation, T1D-EVCs formed vacuoles and lumens but did not sprout (FIG. 8E-F). On day 3, T1D-EVCs encapsulated in non-hypoxic hydrogel had limited tube formation (FIGS. 6E and F). Overall, significantly more complex 3D T1D-EVC network assembly in hypoxic hydrogel compared to non-hypoxic hydrogel was observed.

FIG. 6 shows vascular assembly from T1D-EVCs in hypoxic hydrogel. (A) LM images showing the progression of vascular morphogenesis starting with (i) single-cell vacuole formation, (ii) multiple vacuoles coalesce, (iii) open lumen formation, and (iv) sprouting. Scale bars are 10 μm. (B) LM and (C) confocal 3D maximum projection images of T1DEVCs encapsulated in hypoxic hydrogel for 3 days. Green: phalloidin. Scale bars are 100 μm. (D) Orthogonal view of confocal z-stack showing the presence of lumens in the hypoxic 3D T1D-EVC network. Lumens are labeled with asterisks (*). Green: phalloidin. Scale bars are 100 μm. (E) LM and (F) confocal 3D maximum projection images of T1D-EVCs encapsulated in non-hypoxic hydrogel for 3 days. Green: phalloidin. Scale bars are 100 µm.

FIG. 8 shows encapsulated T1D-EVCs in hypoxic hydrogel and non-hypoxic hydrogel. DO level measured at the bottom of (A) T1D-EVCs in hypoxic hydrogel and (B) T1D-EVCs in non-hypoxic hydrogel over the course of 72 hours. The spikes are caused by media change. In hypoxic hydrogel, (C) vacuole and lumen formation were observed within 24 hours post-encapsulation and (D) most cells started to sprout 48 hours post-encapsulation. In non-hypoxic hydrogel, (E) vacuole and lumen formation were observed within 24 hours of encapsulation and (F) most cells remain rounded with some vacuoles 48 hours post-encapsulation. Vacuoles and lumens are labeled with asterisks. Scale bars are 100 µm.

Three-Dimensional Analysis of T1D-EVC Hypoxic Network.

Figure 7A:
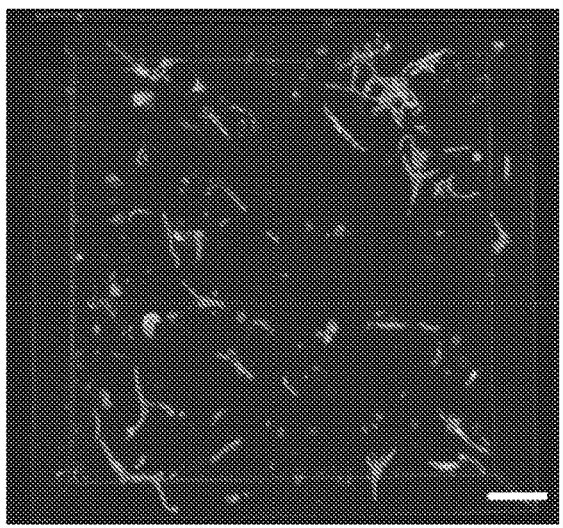
FIG. 7A-7H shows three-dimensional analysis of T1D-EVC network in both non-hypoxic and hypoxic hydrogel.
Figure 7B:
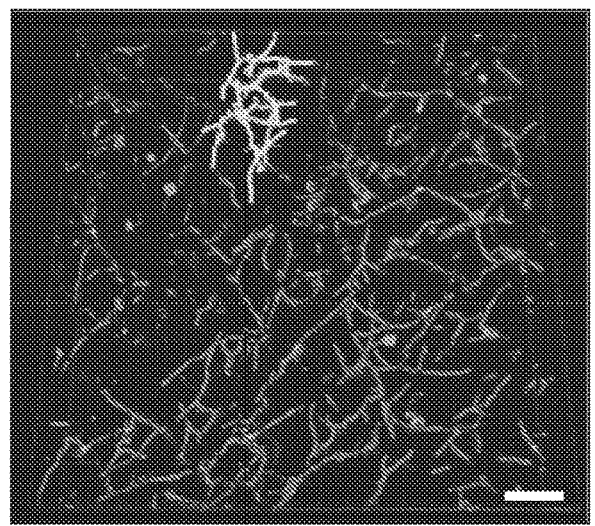
Figure 7C:
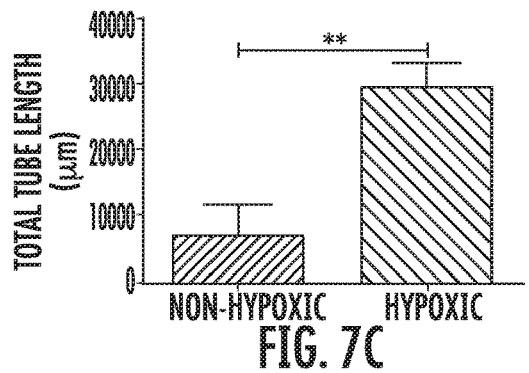
Figure 7D:
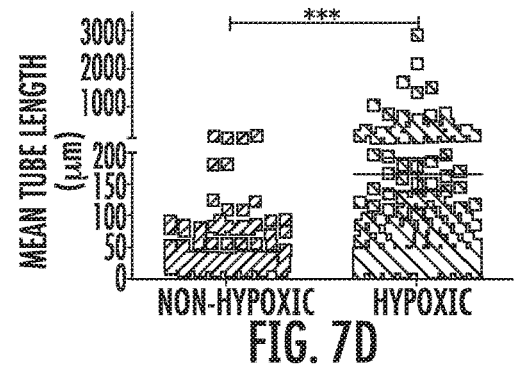
Figure 7E:
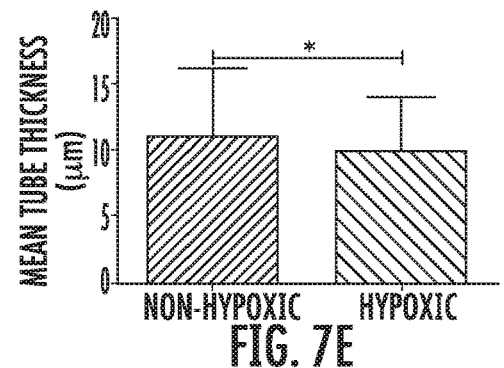
Figure 7F:
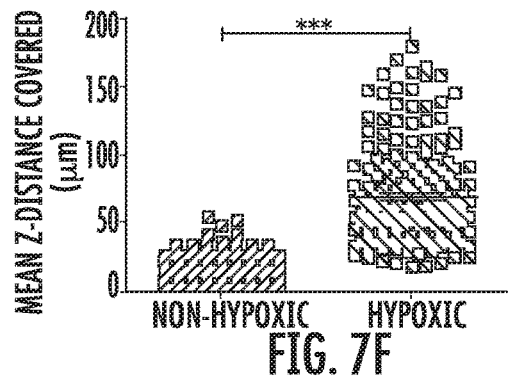
Figure 7G:
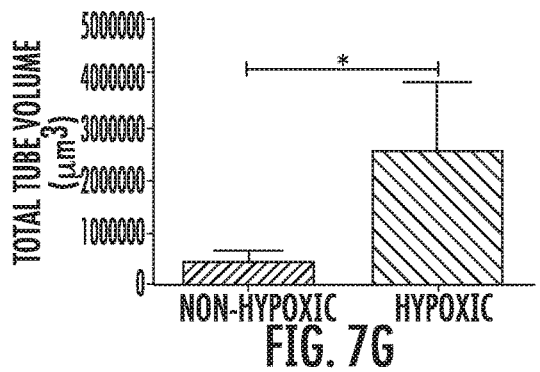
Figure 7H:
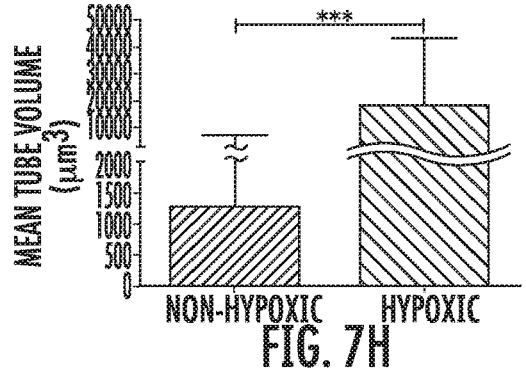

Vascular network quantification is typically performed in two dimensions using 3D projection images of confocal z-stacks, limiting information along the z-axis. To have a more comprehensive analysis of the 3D T1D-EVC hypoxic network formed in the hydrogels, a 3D image analysis was employed. This approach allows for analysis of z-stack images in 3D to provide quantification on the differences between vascular networks formed within non-hypoxic and hypoxic encapsulated T1D-EVCs (FIG. 7A-B). Based on the analysis, a significant difference between the non-hypoxic and hypoxic hydrogel encapsulated T1D-EVCs was observed, especially along the z-axis (n=3). At the same cell encapsulation density and after 3 days in culture, the total combined tube length of the hypoxic hydrogel encapsulated T1D-EVC network is four times longer than its non-hypoxic counterpart. In T1D-EVC hypoxic hydrogel construct, the individual continuous tube length ranges from 10 µm to 3000 µm with an average of 166.82 µm, in comparison to 10 µm to 200 µm with an average of 41.6 µm in the non-hypoxic hydrogel constructs (FIGS. 7C and D). Also, the mean tube thickness of T1D-EVC non-hypoxic hydrogel construct is approximately 1 µm thicker in diameter than the T1D-EVC hypoxic hydrogel construct (FIG. 7E). A unique aspect of 3D analysis is that it provides information of the T1D-EVC network in the z-direction. One astounding effect of hypoxic hydrogel on T1D-EVCs tubulogenesis and network formation is that the network structures are spanning a much larger distance along the z-axis, ranging from 17.2 µm to 179.4 µm, with an average of 68.4 µm in hypoxic hydrogel (FIG. 7F). In comparison, the Z-distance covered in non-hypoxic hydrogel encapsulated T1D-EVC ranges from 2.0 µm to 53.4 µm, with an average of 11.5 µm (FIG. 7F). The total volume covered by T1D-EVC network in each hypoxic hydrogel is $2.5 \times 10^6$ µm$^3$, with an average volume of $1.8 \times 10^4$ µm$^3$ per tube structure (FIGS. 7G and H). On the other hand, the total volume of T1D-EVC network in non-hypoxic hydrogel is $1.3 \times 10^5$ µm$^3$, with an average volume of $1.3 \times 10^3$ µm$^3$. This indicates that T1D-EVCs are responding to the low DO level, which plays a role in stimulating the migratory behavior and ability to form networks in hypoxic hydrogel. In non-hypoxic hydrogel, most T1D-EVC tubes form along the x-y axis, instead of the z-axis, indicating the lack of stimulation and signaling for the migratory behavior of the EVCs.

FIG. 7 shows three-dimensional analysis of T1D-EVC network in both non-hypoxic and hypoxic hydrogel. Representative day 3 confocal z-stack of (A) non-hypoxic and (B) hypoxic hydrogel encapsulated T1D-EVCs analyzed with Imaris Filament Tracer. Green: Phalloidin. Red lines: T1D-EVC tubes/network that are traced and analyzed. Yellow lines: an example of a continuous T1D-EVC network in the hypoxic hydrogel. Scale bars are 100 µm. Multiple aspects of the analysis based on non-hypoxic and hypoxic hydrogel confocal z-stacks are compared and presented on bar graphs or scatter plots: (C) Total tube length; (D) Mean tube length; (E) Mean tube thickness; (F) Mean Z-distance covered in hydrogel; (G) Total tube volume; and (H) Mean tube volume. Significance levels were set at $*p<0.05$, $p<0.01$, and $*p<0.001$.

Diabetes patients suffer from serious chronic health complications as a result of prolonged exposure to the high blood glucose levels. Since most of these complications are related to the dysfunction of ECs and EPCs in the patients, an ideal solution would be an alternative source of adult stem cells (other than the EPCs) for the potential autologous vascular therapy.

Studies have shown that the co-culturing of ECs and murine pericytes or human mesenchymal stem cells are important in sustaining engineered blood vessel network in vivo. In embodiments of the invention, derivation of EVCs consisting VEcad+ cells (early ECs) and PDGFRβ+ cells (early pericytes) from a T1D patient-derived hiPSC is described.

In an attempt to increase VEcad+ cells in the EVC population, the effect of initial cell seeding density and of ROCK inhibitor on enhanced EC fate decision from both healthy and diabetic hiPSCs was determined. Cell seeding density has been an important factor in stem cell culture, whether in maintaining a specific cell type in the differentiated state or in differentiating adult stem cells and iPSCs into a specific cell type. Previous methods have shown that the differentiation propensity of hESCs into pancreatic endocrine cells is favored at high initial seeding density at $5.3 \times 10^4$ cells/cm$^2$, which reached 100% confluency 24 hours after seeding. These methods do not show how to produce populations of cells as described in certain embodiments of the invention. In embodiments of the invention, increased initial seeding density from $5 \times 10^4$ cells/cm$^2$ to $1 \times 10^5$ cells/cm$^2$ provided a significant increase of early EC yield. A similar effect in differentiation culture supplemented with ROCK inhibitor was observed. ROCK inhibitor improved the cell survival and cell attachment during seeding which, in turn created an effect that is similar to increasing the initial seeding density and provided a better EC yield during differentiation. It is also plausible that ROCK inhibition plays a role that is more than increasing the total cell density in the culture. Phosphotase and tensin homolog (PTEN) is activated by Rho/ROCK pathway, which leads to inhibition of protein kinase B (also known as Akt) pathway that regulates cell proliferation, specifically EC proliferation. On the other hand, activation of myosin light chain by Rho/ROCK pathway is known to promote myogenic differentiation including pericyte differentiation. Without being bound by theory, it is believed that the suppression of ROCK in the present differentiation culture may play a role in inducing EC fates.

Since ECs and EPCs isolated from diabetic patients are known to be deficient due to hyperglycemia, it was investigated if T1D-ECs retain any deficits as typical diabetic ECs. Thus, the question was addressed assessing whether the T1D-derived ECs express mature EC markers and behaved as healthy ECs using functional assays such as Matrigel cord formation and TNFα response. It was found that T1D-ECs expressed all necessary markers found and have typical behavior of mature and functional ECs, as in the case of BC1 ECs.

One main advantage of deriving both ECs and pericytes from the same source is that the differentiated early vascular cells are readily available for co-encapsulation in synthetic hydrogel to form a stable 3D vascular network. Using two different synthetic hydrogel systems, it was demonstrated that the T1D-EVCs are capable for forming 3D networks upon encapsulation, paving ways for future research towards potential translational and therapeutic purposes.

Similar to the BC1 hiPSC-derived EVCs, the bicellular EVC population derived from T1D hiPSC formed 3D microvascular network when embedded in engineered HA-based hydrogel. Vacuole formation, coalescing of vacuoles to form larger lumens and sprouting of the T1D-EVCs during the first two days of encapsulation was observed. In the next stage of vascular morphogenesis, microvascular networks formed from cell sprouting and joining with neighboring cells. Overall, the kinetics of morphogenesis was found to be similar between the HA-embedded T1D-EVCs and BC1-EVCs as previously described. This finding indicates that T1D-EVCs respond to cues from the surrounding extracellular matrix to form complete 3D vascular network, which can be harnessed to treat diabetic vascular complications such as the diabetic foot ulcers (DFUs). Shortened healing periods of DFUs have been demonstrated to decrease chances of amputation. Thus, the approach of direct delivery of a microvascular bed encapsulated in synthetic hydrogels could potentially promote and accelerate wound healing in the DFUs.

To further validate the functionality of the T1D-EVCs, a hypoxic hydrogel system was employed. It was demonstrated that T1D-EVCs, like healthy endothelial-colony-forming-cells ECFCs, responded to low DO level in the HI hydrogel, and then, underwent vascular morphogenesis to form 3D EVC networks. The observed mean tube length and thickness of T1D-EVCs encapsulated in hypoxic hydrogel are comparable to those of hypoxic hydrogel encapsulated ECFCs. Altogether, these observations demonstrate that T1D-EVCs are sensitive and responsive to hypoxic environment. In addition, by inducing hypoxia, the hypoxic hydrogels provides a platform for guiding and accelerating 3D EVC network formation in vitro. This is the first time that the formation of EVC network in response to a hypoxic microenvironment has been realized. Overall, this finding demonstrates the ability of T1D-EVCs to respond to hypoxic matrix to form 3D network which can lead to a therapeutic tool for diabetic patients.

In summary, diabetic patients are prone to cardiovascular diseases and wound healing complications due to dysfunctional endothelial progenitor cells under hyperglycemia. HiPSCs serve as a great source for generating patient-specific vascular cells, aiming towards future autologous vascular therapy for diabetics. Embodiments of the instant invention can generate early vascular cells (EVCs), which include endothelial cells and pericytes from T1D-hiPSC. Unlike the isolated diabetic endothelial progenitor cells, the differentiated ECs can be matured and are functional. When encapsulated in synthetic hydrogel, T1D-EVCs respond to matrix cues and self-assembled to form three-dimensional EVCs. Moreover, these EVCs respond to hypoxic microenvironment and undergo vasculogenesis to form complex 3D networks. This is the first example provided to differentiate EVCs from T1D-hiPSC, demonstrate EC functionality and induce vasculogenesis in 3D matrix and under hypoxic conditions. The combination of T1D-EVCs and the synthetic hydrogel system establish a platform that could be useful for therapeutic vasculogenesis in diabetic patients.

Individuals with diabetes exhibit significant impairments in wound healing, which underlies high incidence of diabetic foot ulcers (DFUs), as well as morbidity and mortality associated with this condition. The estimated lifetime risk for developing foot ulcers is 25 percent in diabetics, and more than 14-24% of these patients will require amputation as a result of progressive disease. The current standard of treatment includes debridement of the wound, infection control, and application of various wound dressings to facilitate healing. However, in many cases, using these treatments is not efficient to facilitate ideal healing, as non-healing diabetic ulcers have become a leading cause of non-traumatic amputation in the U.S.

In humans, wound healing is a continuum of processes, which consists of several overlapping stages. These stages include inflammation, cell proliferation, migration, angiogenesis, re-epithelialization, and reconstruction of the extracellular matrix. Specifically, neovascularization and angiogenesis are critical determinants of wound-healing outcomes. Newly formed blood vessels, comprised of endothelial cells (ECs) and supporting cells, such as pericytes, participate in the healing process, providing nutrition and oxygen to growing tissues.

In uncontrolled diabetic patients (both type-1 and type-2 diabetes), constant hyperglycemia can cause dysfunction at several stages throughout the wound healing process. For example, inflammation is prolonged and intensified due to the intrinsic high glucose environment, as the ability of macrophages to remove necrotic cells is diminished. Additionally, perpetual high glucose levels in the blood prevent proper blood flow to the extremities, which causes a lack of oxygen and nutrient supply, thereby limiting angiogenesis and altering the permeability of the vasculature. Importantly, diabetes-induced abnormalities in endothelial progenitor cell function likely aggravates the impairment in neovascularization in diabetic wounds. Thus, patients often suffer from an impaired wound healing process and exhibit non-healing wounds, which consequently can lead to ulcers, especially in the lower extremities.

The present invention provides an approach for wound treatment where biomaterials are used as a scaffold to induce new vascular growth in damaged vasculatures. However, in diabetes patients, who suffer from a slow regenerative capacity, it is imperative to augment the endogenous pathways by delivering the vascular components to upsurge regeneration.

Vascular engineering encompasses rebuilding vessels in vitro within hydrogel matrix, utilizing cues inherent to the synthesized cells or present in the material to regulate the morphogenesis of ECs to create patent microvascular networks for subsequent transplantation. The inventors have engineered hyaluronic-acid (HA) hydrogel material to induce vasculogenesis of endothelial colony forming cells (ECFCs) resulting in functional human microvascular networks in a deliverable matrix. The inventors demonstrated the derivation of early vascular cells (EVCs) from human induced pluripotent stem cell (hiPSC). These hiPSC-EVCs can mature into ECs and pericytes and self-assemble to functional multicellular microvascular networks in the HA hydrogels. The generation of vascular networks containing pericytes is highly relevant given its likely importance in wound healing in both normal and diabetic environments. Moreover, hiPSCs might be less susceptible to diabetes-induced impairments, which further increases their attractiveness as a source for vascular cells for diabetic wound healing. In that context, the inventors derived EVCs from hiPSCs reprogrammed from type 1 diabetic (T1D) patients and demonstrated their functionality and ability to form networks in HA hydrogels as well as in response to hypoxic conditions. Engineering vascularized constructs in which stem cell-derivatives pre-formed vascular networks in a deliverable matrix offer unmet opportunities to treat diabetic wounds. It is believed that engineered vascularized constructs of the present invention would survive implantation into diabetic wounds and integrate with the diabetic host to reestablish blood flow more efficiently to improve the wound healing rate of diabetic ulcers compared to controls. In this light, the inventors have examined the effectiveness of both ECFCs and hiPSC-EVCs as the cellular bases for these constructs, given the potential advantages that each offers, and they have compared the effectiveness of diabetic and non-diabetic hiPSCs. Immunodeficient Diabetes Mellitus Wound Mouse Model. As present invention demonstrates that AHA hydrogels can be engineered to support the formation of functional human microvascular networks from either ECFCs or EVCs. Such engineered human microvascular constructs can be delivered to the site of deep burn injury model, survive transplantation and integrate with the host vasculature. A mouse model was used to investigate the therapeutic potential of our engineered human microvascular constructs in diabetic wound healing. The STZ-induced diabetic mouse model is one of the most extensively used models in type 1 diabetic (T1D) wound repair and provides a deep understanding of diabetic wound healing. Since the inventors are delivering a human cellular network, they first developed a robust immunodeficient diabetic rodent model in order to investigate therapeutic potential of our microvascular constructs.

Standard protocol suggested by Animal Models of Diabetic Complications Consortium for inducing diabetes in mice using streptozotocin were followed. The inventors tested both a single large STZ dose (150 mg/kg body weight) and multiple low STZ doses (50 mg/kg body weight). Both methods successfully induced diabetic nude mice, however, the single large dosage had a higher mortality rate after 14 days from the time of the first injection (data not shown). The higher dosage would have limited the length of the study, thus we opted for multiple low dose induction protocol (FIG. 11A). Animals received daily STZ injection for 5 days. Their blood glucose levels rose around one week following the first injection (FIG. 11B). Noticed were variation of drug tolerances in different batches of animals. However, more than 80% of all animals receiving STZ were successfully induced (not shown). Mice maintained their weight during the course of the experiment (data not shown).

The inventors next aimed to mimic diabetic wounds in order to test the therapeutic potential of the engineered human vascular constructs. Following successful induction of diabetes mellitus, confirmed by 2 consecutive glucose readings separated by 48 hours, the inventors created two full-thickness, 6 mm punch biopsy wounds on each side of dorsal midline of the animals. One served as a treatment group and the other served as a paired non-treatment control. Human vascular network constructs were generated during the induction period. Constructs were placed into the wounds and layered with Tegaderm to enable their placement and to maintain a moist and sterile environment during wound healing (FIG. 11C). This setup also enabled us to observe and monitor skin closure as well as to perform blood flow measurement during wound healing.

In Vitro Microvascular Networks from Various Cell Sources.

Figure 12A:
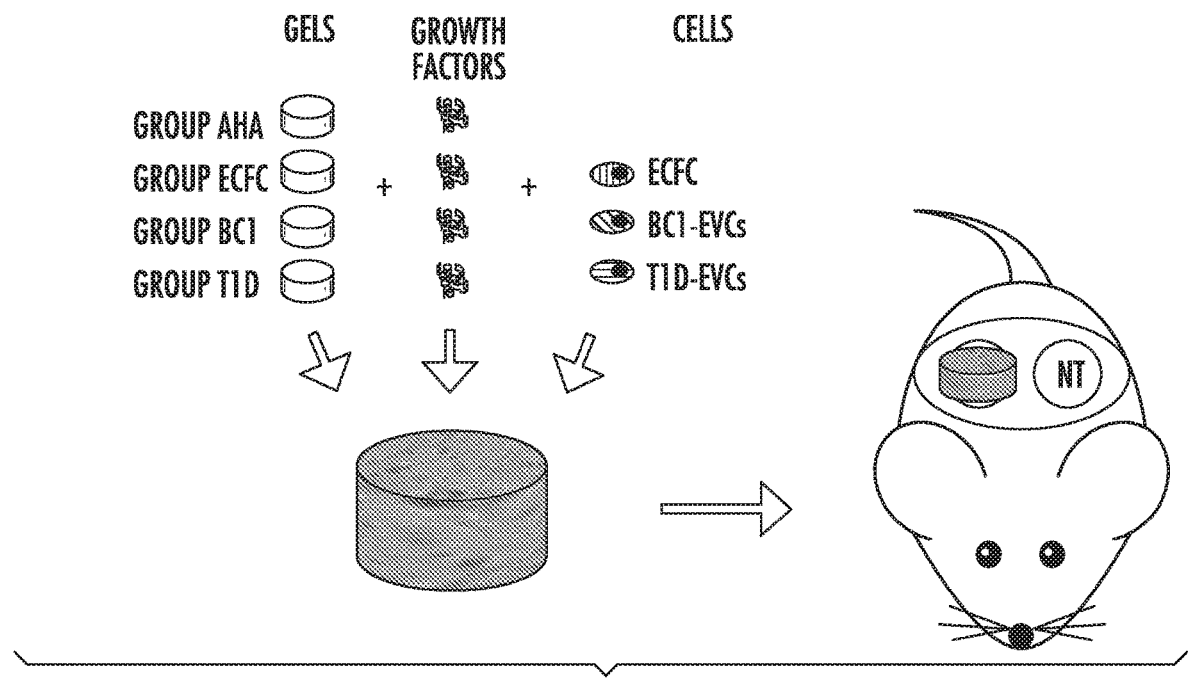
FIG. 12A-12B shows experimental groups and in vitro engineered human vascular constructs. (A) Treatment groups for DFU using acellular (AHA) and cellular (ECFC, EVC-BC1, EVC-T1D) vascularized constructs. NT=no treatment (B) in vitro cultures of the microvascular constructs on days 1 and 3. Vacuoles are marked as red arrowheads and capillary structures are marked as yellow arrowheads. Scale bar is 100 μm.
Figure 12B:
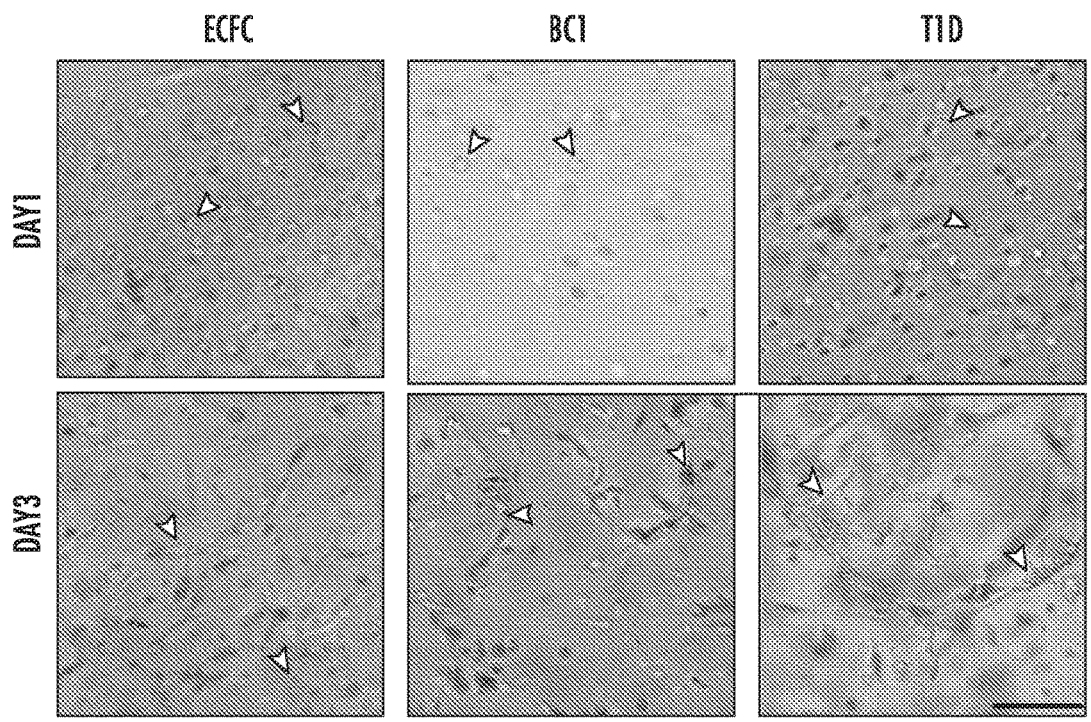

Established is a robust and controlled approach to derive EVCs, from hiPSCs sourced from healthy donor (BC1) and Type 1 diabetic patient (T1D). Together with established adult progenitor cell source (ECFCs), the inventors examined 4 different groups (FIG. 12A). Groups ECFC, EVC-BC1 and EVC-T1D were of AHA vascularized constructs generated with corresponding cell sources. The acellular construct group, Group AHA, were treated with AHA hydrogels without cells. All constructs were cultured under the same conditions in vitro for 72 hours. In the cellular constructs, vacuole formation was observed on day 1 followed by capillary-like microvasculature (multicellular network structures longer than 100 µm) formation on day 3 for all three cellular treatment groups (FIG. 12B).

Macroscopic Wound Closure and Blood Flow Profile.

The progress of wound closure for all groups at various time points was closely followed (FIG. 13). Planetary photos following treatment found that after 7 days, the largest open wounds remained in the no-treatment (NT) wounds, followed by wounds treated with the acellular AHA constructs. Complete wound closure occurred within 14 days (FIG. 13A). When treated with acellular AHA constructs, wounds closed earlier than wounds that received NT. However, during the 2-week period, all cellular groups showed significantly accelerated wound closure when compared to both acellular AHA constructs and NT controls (FIG. 13B). Exploring wound size along the treatment period we noticed that the trend in healing was similar among the wounds treated with the constructs, either acellular or cellular groups, and significantly different from NT group. Interestingly, although no significant differences were observed among the cellular treatment, ECFC constructs healed in a faster rate than acellular AHA group. (FIG. 13C).

Blood flow measurements were performed along the treatment period. Measurements on day 3 were neglected since the machine was reading the muscle layer underneath the wound bed. On day 5, significantly higher blood flow was observed in ECFC, BC1 and T1D groups when compared to AHA or NT wounds. Interestingly, on day 7, delayed increase in blood flow was found in wounds treated with AHA. Notably, on day 10, all wounds treated with cellular constructs (ECFC, EVC-BC1/T1D) had higher blood flow readings when compared with wounds treated with AHA and NT. On day 14, wounds treated with ECFCs and EVC-BC1 had significantly higher blood flow when compared with AHA and NT. Interestingly, significant differences between ECFC and BC1 treatment groups was not observed at all time points (FIG. 13Di). Examining the change in blood flow along each of the treatment groups, it was observed that wounds treated with EVC-BC1 or EVC-T1D seem to have a decrease in blood flow on day 14, but these were found statistically insignificant compared to blood flow on d10 (FIG. 13Dii).

Wound Healing Rate Analysis.

In the analyses described above, a possible difference in the progression of healing among the cellular treatment groups was noticed. To further characterize this, the inventors quantitatively model the progression in wound healing to determine the differences among the different groups. Healing of wounds has been extensively studied using mathematical modeling. In the present experiments, the wound closure profiles closely matched the profile of a logistic function. Thus, the inventors utilized a mathematical equation that represents the time course of the healing to determine the underlying biological events. The inventors chose a logistic growth curve to macroscopically model their wound healing profile, which not only provided an accurate fit, but also a biophysical significance and predictive capability.

The equation below is written as for a non-linear regression fit, where y represents the progression of wound healing (in terms of percent skin closure), which corresponds to the open wound size % from FIG. 3A. t represents the time post implantation. The logistic growth equation used for modeling the wound healing is as followed.

$$y = \frac{100}{1 + e^{-\alpha(t-\beta)}}$$

Figure 14A:
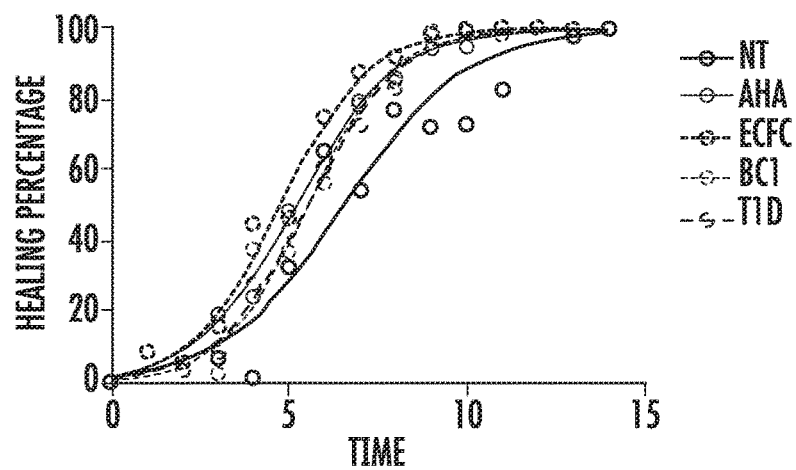
FIG. 14A-14C shows wound healing model profile, velocity and acceleration. (A) Wound healing fitted model. Circles represent mean value of wounds healed at given time point from experimental results. Color lines are numeric value from the fitted model. (B) Velocity profile from first derivative of fitted model and (C) Acceleration profile from second derivative of the fitted model for assessment of healing of diabetic wound for each of the treatment groups.
Figure 14B:
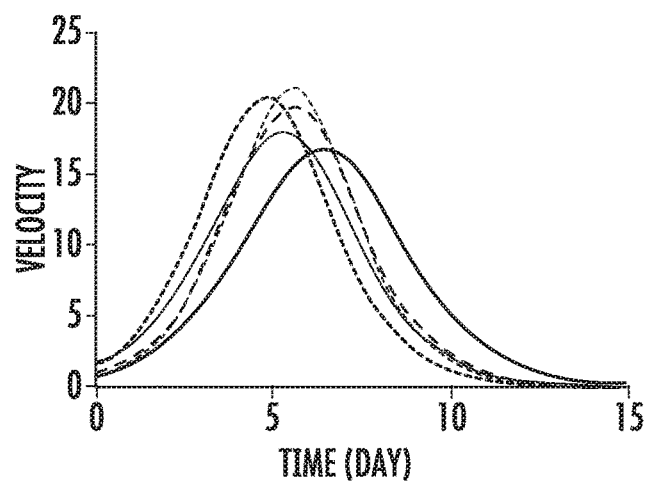
Figure 14C:
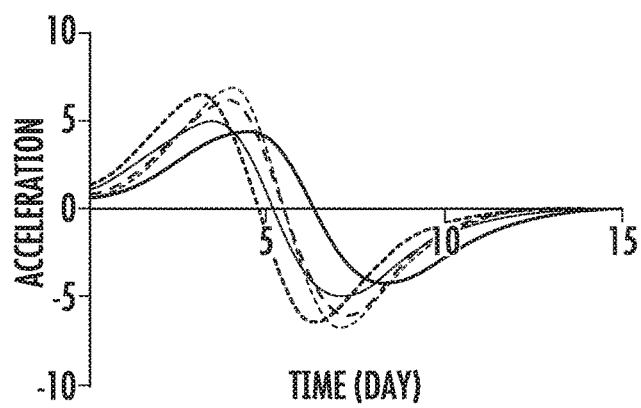

The computed regression fit parameters are shown in Table 2. Goodness of fit of the regression model to our diabetic wound healing data is reported by the given R-squared value (FIG. 14A). The parameter α stoichiometrically represents the intrinsic skin closure rate and the parameter β indicates the time to reach the maximum closure rate. Different treatment groups were compared by analyzing the parameters through a t-test (Table 2). Computing parameters α and β generates velocity (first derivative) and acceleration (second derivative) profiles (FIG. 14B-14C) to visualize the closure rate profile and the healing acceleration profile. It was found that all three cellular treatments groups (ECFC, EVC-BC1 and EVC-T1D) healed at a similar rate. In other words, there were no significant statistical differences between the healing rates of the cellular treatment groups, which corroborate the experimental data. All cellular treatments groups reached maximum peak closure rate significantly sooner when compared to the acellular AHA and NT groups (Table 2). Wounds treated with ECFCs had the earliest maximum closure rate when compared with EVC-BC1 and EVC-T1D treatments, however, there were no significant difference between wounds treated with EVC-BC1 or EVC-T1D in terms of both healing rate and the time to reach maximum rate. Wounds treated with acellular AHA constructs healed at a more accelerated manner (less time to reach maximum) and also greater in magnitude compared to the NT wounds (FIG. 14B-14C).

Microscopic Wound Analysis.

Wound progression histologically was found at early wound healing on day 3 and 7. It was observed that wound closure described in the previous sections is consistent to the microscopic analysis as indicated by closer wound leading edges of wounds treated with vascularized constructs compared to NT group (FIG. 15A). Moreover, eschars, which formed in all treatment groups, were the thickest in the NT group followed by the AHA group (FIG. 15A). Finally, compared with cellular treatment groups, bulk hydrogel pieces can still be found in the wounds treated with AHA construct whereas hydrogels of the vascularized constructs were mostly degraded (FIG. 15A).

Quantification analysis revealed that on day 3, an enhanced granulation tissue formed in all treatments with a thinner granulation tissue response in the NT group that increased by the end the first week of treatment. Moreover, it was found that after 7 days of treatment, granulation layer in the vascularized constructed groups regressed and was thinner than the granulation layer in the AHA or NT groups (FIG. 15B), suggesting rapid healing of the wounds treated with vascularized constructs.

Macrophage Infiltration.

Figure 16A:
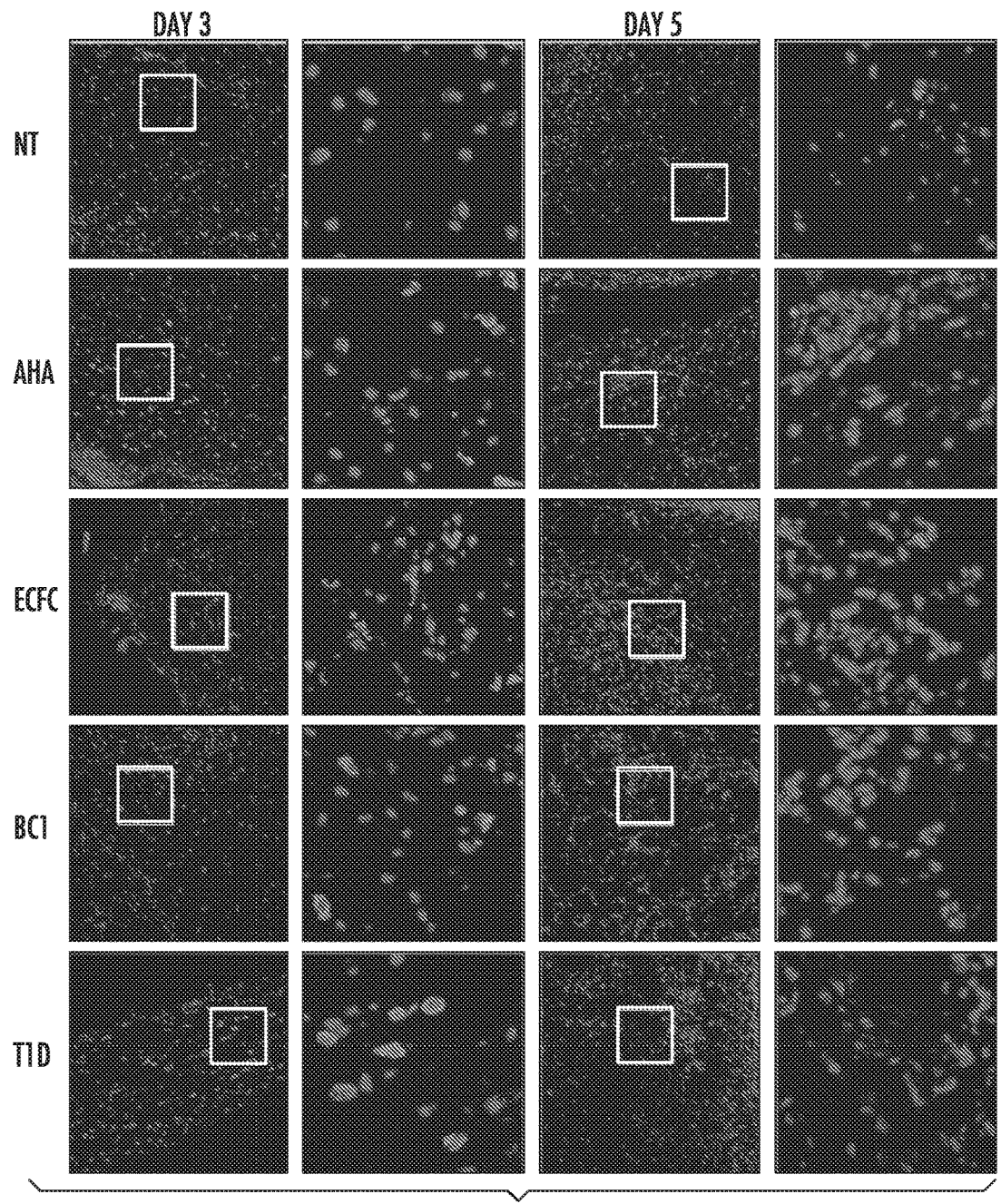
FIG. 16A-16B. Macrophage response during healing. (A) Representative day 3 and 5 images of immunofluorescence stain for macrophage (red; nuclei in blue) and (B) Quantification of macrophage density in the wound. N=3 each. Scale bar is 100 μm.
Figure 16B:
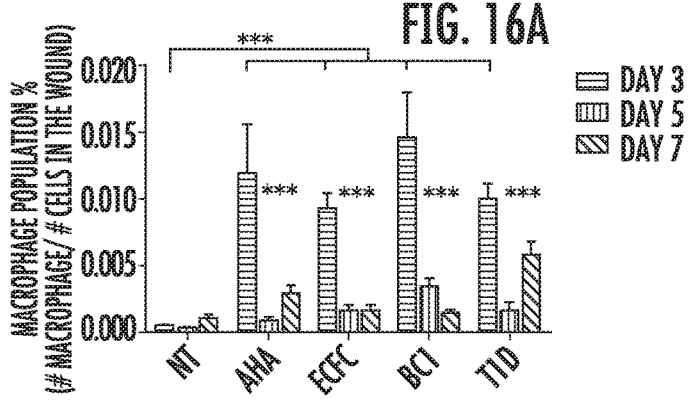

Activation of inflammatory cells plays an important role in recruiting blood vessels. It was investigated how the macrophages respond to the constructs in the diabetic wound model. Immunofluorescence staining revealed cluster of macrophages on day 3 of treatment in all construct groups with signal reducing on day 5 (FIG. 16A). Quantification analysis further showed a significantly higher percentage of macrophage recruited to the wound area on day 3 for all wounds treated with hydrogel compared with NT. There were no significant difference between ECFC, BC1 and T1D treatments (FIG. 16B). The number of macrophages significantly reduced by day 5 with similar trend observed in all wounds treated with the construct, suggesting that the endogenous foreign body response accelerated healing process.

Vascular Density and Human Vascular Integration During Diabetic Wound Healing.

Figure 17A:
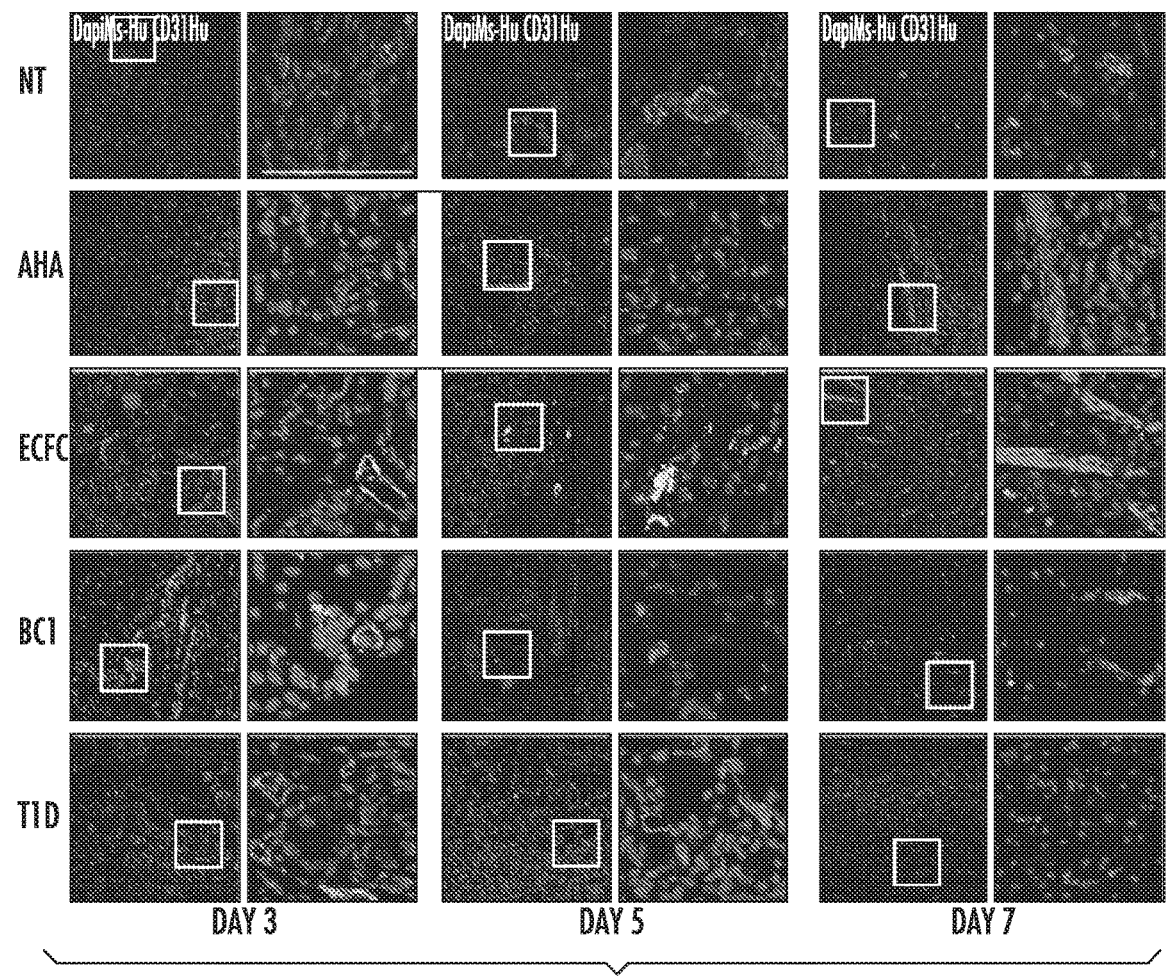
FIG. 17A-17B shows wound vasculatures along the first week of healing. (A) Representative immunofluorescent images of wound vasculatures in different groups. Three types of vessels are shown here. Green indicated human vessels origin. Red marked primary mouse vasculatures or human EC and yellow (overlay of red and green) indicates human endothelial cells only. DAPI for nucleus. (B) Quantification of two types of vasculatures (Mouse and human vessels) after fluorescent immunohistochemistry staining on the paraffin. N=3 each. Scale bar is 100 μm.
Figure 17B:
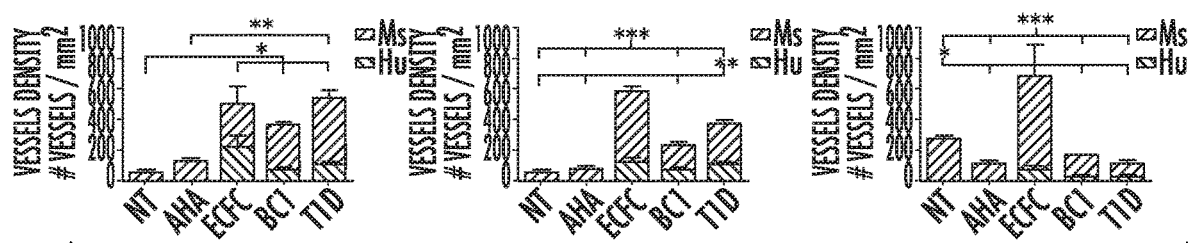

The vasculatures was quantified with respect to both the overall vascular density as well as their human or murine origin, to better determine their contribution to the different rate of wound closure in different treatment groups. Histological sections were stained with anti-mouse CD31 (red) for mouse and human ECs; and anti-human IgG (green) for human cells (FIG. 17A). It was found that on day 3, there was higher mouse vascular density for all cellular treatments compared to AHA and NT. It was found that compared to AHA group, the NT group had an increase in mouse vessel density on day 7, suggesting a delay in recruiting host angiogenesis in the NT group. Among the cellular treatment groups, ECFC group had a significantly higher overall vessel density on day 7. In addition, in all the cellular treatment groups, human vessel regressed by the end of the first weeks of treatment with ECFCs exhibiting residual human vessels at this time-point (FIG. 17B).

Figure 18:
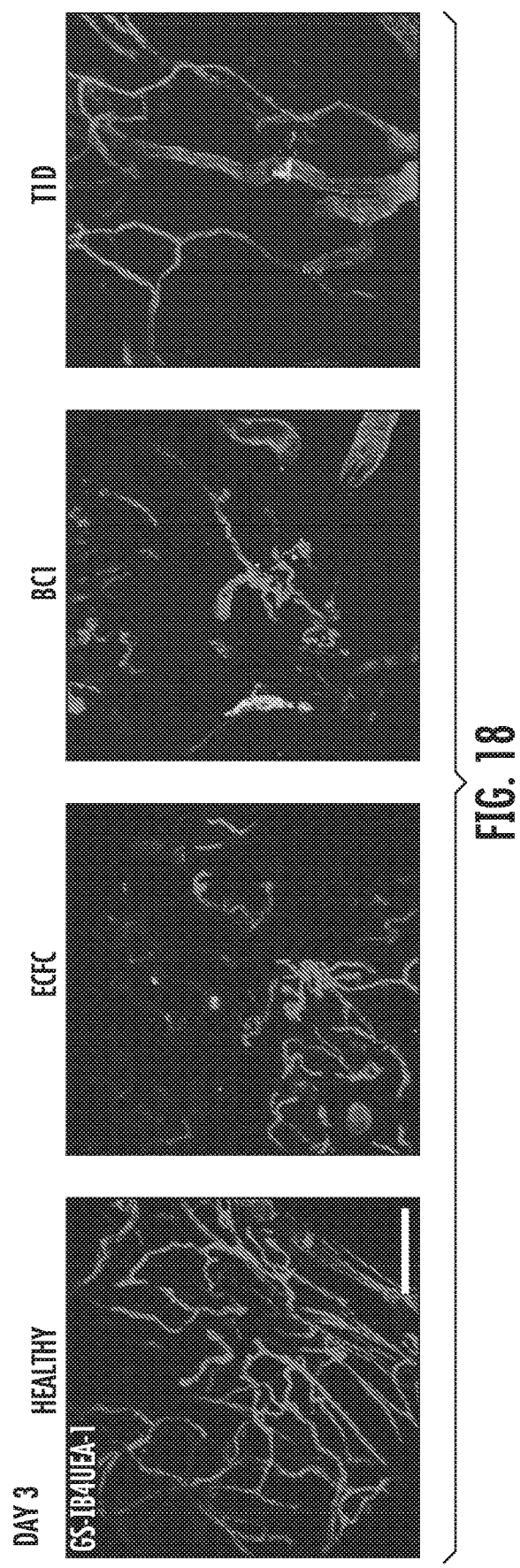
FIG. 18. Functionality of the chimeric vasculatures on day 3. Representative images of 3D confocal maximum intensity projection of the wound vasculatures. Healthy vasculatures shown on the left. Animals were tail vein injected with lectin (Green-UEA-1 for human and Red-GS-IB4 for mouse). Diffusion allows perfused blood vessels to be stained. There are all green signal found in the cellular treatment groups. Scale bar is 100 μm.

To examine the integration of the transplanted human vasculature with the host vasculature, both the human and mouse lectin solutions were injected via tail vein. It was found that on day 3, not only the invaded mouse vasculature are functional, but some of the transplanted human vasculature were found to be perfused (FIG. 18).

The inventors have utilized STZ, a compound that has toxicity targeting the pancreatic β cells to establish an immunodeficient diabetic wound healing model. Streptozotocin (STZ) is a glucosamine-nitrosourea compound having the following structure:

TABLE 2

Wound healing fitted curve parameters and regression fitness

| | NT | | AHA | | ECFC | | BC1 | | T1D | |
|---|---|---|---|---|---|---|---|---|---|---|
| | Value | SD | Value | SD | Value | SD | Value | SD | Value | SD |
| α | $0.591^{ebta}$ | 0.119 | $0.720^{ebm}$ | 0.037 | $0.818^{na}$ | 0.067 | $0.844^{na}$ | 0.126 | $0.793^{na}$ | 0.054 |
| -β | $6.560^{ebta}$ | 0.377 | $5.233^{ebm}$ | 0.081 | $4.770^{bna}$ | 0.113 | $5.541^{ena}$ | 0.199 | $5.532^{ena}$ | 0.094 |
| $R^2$ | 0.922 | | 0.996 | | 0.99 | | 0.972 | | 0.995 | |

Significant difference (p < 0.05) at each column when compared to group NT(n) AHA(a) ECFC(e) BC1(b) and T1D(t)

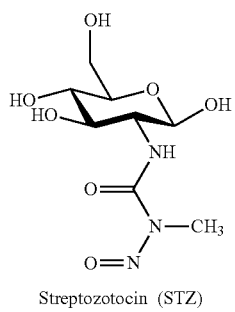

Streptozotocin (STZ)

The inventors noted that the survival of nude mice following STZ treatments posed a greater challenge when compared to the wild type mouse, and literatures has shown the efficiency of induction could also vary with different methods of induction. The inventors have shown with a one-time high dose injection method, nearly 100% of mice develop diabetes within a week, however, the high dose also led to a high mortality rate 1 week after STZ injection and animals fail to survive past week 2. The inventors also determined that using multiple low dose injections provided optimal diabetes induction results, with low mortality rates and a relatively high rate of successful induction.

To study wound healing in mouse model, many approaches have been developed; one of the methods that has been extensively utilized to replicate human physiology is the splint model. In the splint model, a circular splint, typically made of silicon, is attached with super glue and sutures on the uninjured skin around the wound to prevent wound contraction. This model addresses the contraction issues, which are a major difference between the human and rodent healing mechanisms. For diabetic wound healing, the splint wound was mainly used to test wound healing on the db/db mouse strain. This specific strain has a baseline weight higher than many other mouse strains, resulting in sluggish and slow movement of the animals which allow the splint to stay in place and intact. The inventors tested the splint model in their STZ-induced nude mice and found that the splint lost its adherence after 5 days post operation due to the active nature of the nude mice. The usage of instant glue to better adhere the splint to the skin promoted scratching and further reduced the adherence of the splint after the glue lost its adhesiveness. Consequently, the splint was only left intact with sutures to the mouse skin. However, we found that here was no significant difference in the contraction rate between splinted vs. non-splinted wounds (data not shown). A possible explanation is that the combination of betadine and Tegaderm layered to seal the wounds treated with the hydrogel constructs acted in a similar manner as the silicon splint. As a result, the inventors simplified the procedure and treated the wounds without applying the splint, assuming the contraction rate remained the same magnitude throughout all experimental groups.

After establishing the diabetic wound healing model, the inventors generated vascularized constructs in AHA hydrogels with the selected cell sources. The inventors showed that all ECFCs and derived EVCs from hiPSC of BC1 and T1D undergo vasculogenesis to form microvascular structures using their established protocols. Interestingly, there were no apparent differences in the formation and properties of the vascular networks formed from healthy or T1D-hiPSCs. Following wound treatment, we closely monitored the healing process. Acellular treatment with AHA alone enhanced the healing compared to NT. Vascularized constructs also enhanced healing with ECFC constructs inducing healing in the fastest rate. Examining the blood flow profiles, we found that the presence of implanted microvasculature facilitated faster blood perfusion, especially during the first week compared to acellular AHA constructs and NT. Interestingly, throughout our studies, the inventors could not detect differences between vascularized constructs from healthy and T1D-hiPSCs. This complement the in vitro finding, suggesting that reprogrammed hiPSCs might be less susceptible to diabetes-induced impairments. It has been demonstrated that epigenetic memory such as DNA methylation markers exists in low levels (<5%) in iPSCs and are further reduced over passages. Thus, it is reasonable to speculate that epigenetic changes due to hyperglycemic conditions are reversed with reprogramming, enabling the derivation of functional vascular derivatives. Given the current knowledge suggesting that diabetes compromises endothelial progenitors, the results of the present invention highlight the promise of using hiPSCs for autologous therapies.

While the inventors could observe some differences in the treatment with the cellular constructs, suggesting that ECFCs support better healing compared to hiPSC-EVC constructs these were not statistically significant. To further characterize the healing process, the inventors used a nonlinear logistic growth model to fit the diabetic wound healing profile. It allowed the inventors to compare the healing progression of the wounds between treatment groups. The inventors used a supermacroscopic approach. This approach focused on the mathematical description, in which the interactions are based on the recorded data at the tissue level, where in the present case is the size of the healed wound as determined using photometric measurements. We found that wounds treated with vascularized constructs healed at a faster rate. Moreover, ECFC had the earliest maximum closure rate, although both EVC-BC1 and EVC-T1D also yielded significant improvements in closure rate. Importantly, there were no significant differences between wounds treated with EVC-BC1 or EVC-T1D. In the case of treatment with acellular AHA constructs, wounds still healed faster than NT. This could be attributed to the hydrogel providing a scaffold for cell migration towards the wound site, thereby facilitating healing. This increased wound healing response may also have been due to the growth factors encapsulated in the hydrogels, which are known to activate wound healing pathways. It is worth noting that the present approach poses limitations when compared to a microscopic approach where the variables and relations were constructed at the cellular or molecular level. As a result, the inventors do neglect the individual cellular mechanisms during wound healing. The inventors can then only make indirect observations of relationships between the experimental data and our experimental groups. This analysis limits the inventors to draw direct connections at a microscopic level, rather than at a macroscopic level. However, this supermacroscopic strategy is sufficient to provide quick and direct insight into the outcomes of our different treatments.

Using histological analysis, the inventors found that the granulation layer rapidly formed and regressed in all vascularized constructs treated wounds, while was delayed in the acellular AHA hydrogel and NT groups. As angiogenesis is critical to support newly formed granulation layer, this may explain the rapid increase in blood flow observed in the cellular treatment groups. Moreover, the wounds treated with the acellular AHA hydrogel had non-degraded hydrogels remained in the wounds, which may have hindered the blood perfusion towards the center of the wound. The inventors next found an onset of macrophage infiltration to the wound area on day 3 in all the hydrogel treatment groups without significant difference among them, but not in the NT groups. As macrophages produce growth factors that induce and accelerate wound healing, the data suggests that the hydrogel scaffold trigger macrophage migration to the wound area, which further facilitate hydrogel degradation and neovascularization.

The inventors analyzed the mouse and human blood vessels along the healing and found that the cellular constructs induced earlier and more host angiogenesis than observed in the wounds treated with acellular AHA construct or NT groups. It may be that secreted factors from the transplanted human vasculature triggered this rapid and extended host angiogenesis. Interestingly, the inventors found that ECFC-vascularized constructs not only induced the highest host angiogenesis but also the transplanted ECFC vasculature retained in the wound area in highest amounts compared to hiPSC-vasculature. The inventors speculate that the ECFCs generated more robust and maybe even more mature vascular networks compared to the early nature of the hiPSC-derivative networks. This emphasizes the importance and potential of future technical improvements that allow generating vascular networks more efficiently and with greater maturation from hiPSC-EVCs prior to their application to diabetic wounds. Nonetheless, all implanted human vasculatures from the three different cell sources all showed rapid integration with the host vasculature.

The inventors concluded that when compared with acellular treatment, the present stem cell engineered vascularized constructs facilitated rapid wound healing through accelerated healing progress. The inventors propose the following sequence of events occurring with the therapy of the present invention: transplanted cellular constructs accelerate the recruitment of host macrophages to the matrix and rapid integration of the human vessels into the wound; these in turn possibly increase local angiogenic factors from both the macrophages and the newly integrated vessels (including pericytes) leading to an increase in host neovessels and rapid wound closure.

The wound healing system of the present invention has several limitations that would need to be addressed prior clinical testing. First is the use of xeno free culture condition that is necessary for clinical use. Moreover, the STZ-injected animal model of the present invention mimics T1D conditions. Unlike T1D where the pancreas completely stops producing insulin, type 2 diabetes (T2D) is associated with hyperinsulinemia, which can cause extensive insulin resistance and inflammation in the peripheral tissues and vasculatures. In addition, it has been shown in a mouse hind-limb ischemia model that the recovery of blood flow after ischemia was delayed and less effective in T2D due to more severely diminished capillary/myofiber ratio and arteriolar size caused by attenuated eNOS expression in ischemic tissue and endothelial progenitor cells. The inventors have shown that the incorporation of endothelial progenitor cells into tubular structures was less effective in T2D. Therefore, immunodeficient T2D animal models are needed to determine wound healing outcome on this diabetic population. However with the present findings, the inventors propose a potential therapeutic strategy using allograft or autologous vascularized constructs to treat T1D wounds with possible application on diabetic foot ulcers. This integrated approach, in which a patient-derived functional microvasculature is incorporated into a modifiable and deliverable matrix, may have vast ramifications for diabetic wound healing.

Oxygen-Controllable and Hypoxia Inducible Hydrogels of the Present Invention.

The oxygen Controllable and Hypoxia-Inducible Hydrogels are described in U.S. application Ser. No. 14/536,392, filed Nov. 7, 2014. HI hydrogels of the invention can be generated with various phenolic agents (phenol molecules), such as ferulic acid (FA), tyramine (TA), 4-Hydroxyphenylacetic acid, 3-(4-Hydroxyphenyl)propionic acid, Dopamine, Norepinephrine, epinephrine, and their derivatives. Such phenolic agents include the structures in Table 1.

TABLE 1

Phenolic Agents

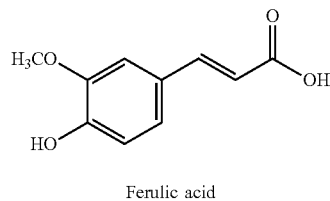

Ferulic acid

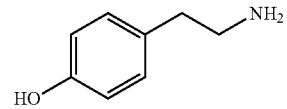

Tyramine

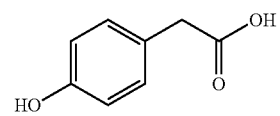

4-Hydroxyphenylacetic acid

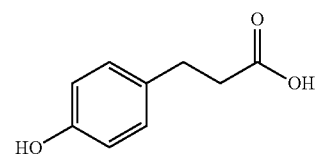 [SMILES: O=C(O)CCc1ccc(O)cc1]

3-(4-Hydroxyphenyl)propionic acid

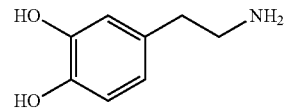 [SMILES: NCCc1ccc(O)c(O)c1]

Dopamine

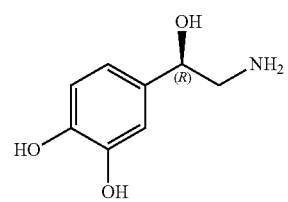

Norepinephrine

TABLE 1-continued

Phenolic Agents

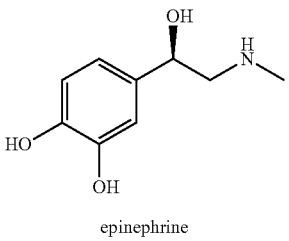

epinephrine

The novel HI hydrogels can be generated from natural or synthetic polymers as the polymer backbone. Examples of natural or synthetic polymers include collagen, gelatin, chitosan, heparin, fibrinogen, hyaluronic acid, chondroitin sulfate, pullulan, xylan, dextran, and polyethylene glycol as well as their derivatives. Gelatin (Gtn) is one preferred polymer backbone due to its cell-response properties, including cell adhesion and proteolytic degradability, which are critical in vascular morphogenesis (Hanjaya-Putra, D. et al., *Blood,* 2011; 118:804-815; Davis, G. E. et al., *Circulation research,* 2005; 97:1093-1107). Gtn provides relatively simple functionalization with for example, FA, for the formation of intramural hypoxia for both in vitro and in vivo vascular inductions. Dextran is a further preferred polymer backbone, used in conjunction with a hydrophilic linker such as polyethylene glycol (PEG) due to modifiability, bioactivity and hydrophilicity, as well as the similarity of the properties to those of various soft tissues. The high content of hydroxyl functional groups in the Dex molecule allows the Dex to be converted or modified easily with other molecules. A chain of Dex polymer includes three hydroxyl groups per repeat unit, which can allow for a high degree of substitution (DS) of target molecules (Jin, R. et al., *Biomaterials* 2007, 28, 2791). In addition, Dex has excellent water solubility that enables easy control of the precursor solutions. Some polymers may incorporate adhesion sites, such as Arg-Gly-Asp, and additional degradability features, such as MMP-sensitive peptides, depending on the application (Cuchiara, M. P. et al., *Advanced functional materials,* 2012; 22:4511-4518; Khetan, S. et al., *Nature materials,* 2013; 12:458-465; DeForest, C. A. et al., *Nature materials,* 2009; 8:659-664).

Methods for Oxygen Concentration Gradient Collagen Gel.

In one embodiment, gradient collagen gels are prepared from commercially available rat tail collagen. A tissue culture dish is coated with polyethylenimine (PEI) and glutaraldehyde to increase adhesion to the gel. A combination of 1 M sodium hydroxide (NaOH), M199 10×, M199 1×, and collagen are mixed at a ratio of 1 part NaOH, to 3.15 parts M199 10×, to 68.0275 parts M199 1×, 27.0125 parts collagen (when the starting concentration of collagen is at 9.15 mg/mL). The solution is then incubated on ice as previously described. (NGUYEN-NGOC, K. V. & Ewald, A. Mammary ductal elongation and myoepithelial migration are regulated by the composition of the extracellular matrix. *Journal of microscopy* 251, 212-223 (2013)).

The collagen gel solution is then mixed with sarcoma cells at a concentration to achieve a final concentration of 2.5 mg/mL of collagen and 2 million cells/mL. The hypoxic gradient is achieved by manipulating the principles of Fick's first law:

$$J = D\frac{\partial c}{\partial z} + R$$

Where J is the flux of oxygen through the gel, D is the diffusion coefficient of the gel, dc/dz is change in oxygen concentration per change in height, and R is the cell oxygen consumption rate. By controlling the vessel that the gel is placed in (i.e. polystyrene tissue culture well) we can minimize the diffusion into the hydrogel through the sides and bottom, and only have oxygen transport through the top of the gel. The diffusion of oxygen through the top of the gel is balanced by the consumption oxygen by the cells, allowing a hypoxic gradient to be maintained.

Examples, Methods hiPSCs expansion and differentiation. Human iPSC lines BC1, T1D H2.1, C12-GFP, and 1018S (passages 25 to 50; BC1 from Dr. Linzhao Cheng (JHU), T1D H2.1 from Dr. Shuibing Chen (Weill Cornell Medical College), C12-GFP and C12-RFP are hiPSC lines received from Dr. Guo-li Ming (Johns Hopkins Medical Institutions), and 1018S is a previously characterized and isolated T1D-hiPSC line from Dr. Dieter Egli (Columbia University)) were cultured as previously described. UTHIF2a was received from Dr. Linzhao Cheng. Cell lines were routinely examined for pluripotent markers using immunofluorescence staining and flow cytometry analysis for TRA-1-60, TRA-1-81, SSEA4, and Oct4. Human iPSCs (T1D H2.1 or BC1) were collected through digestion with ethylenediaminetetraacetic acid (EDTA; Promega, Madison, Wis.), separated into an individual cell suspension using a 40 μm mesh strainer (BD Biosciences), and plated onto collagen IV (Trevigen) coated plates at a concentration as follows. Original differentiation condition at $5 \times 10^4$ cells/cm². Optimized conditions: (i) increased cell seeding density condition at $1 \times 10^5$ cells/cm²; (ii) ROCK suppression condition at 5×104 cells/cm2 with 10 μM ROCK inhibitor Y-27632 (Stemcell Technologies). During mesodermal induction, cells were cultured in a differentiation medium composed of alpha-MEM (Invitrogen Carlsbad, Calif.), 10% FBS (Hyclone) and 0.1 mM β-mercaptoethanol (β-ME) as previously described. In early vascular differentiation, cells were cultured in endothelium growth medium (Promocell) supplemented with 50 ng/mL VEGF (R&D) and SB-431542 (Sigma-Aldrich, St. Louis, Mo.), thereafter, called high VEGF media.

Flow Cytometry.

Flow cytometry was performed as previously described. Briefly, cells were incubated with FITC or PE-conjugated antigen specific antibodies for markers outlined in the text (Table 1). All analyses were done using corresponding isotype or no stain controls. Forward-side scatter plots were used to exclude dead cells. User guide instructions were followed to complete the flow cytometry analysis via CellQuest Pro software (BD Biosciences).

Immunofluorescence and Imaging (2D and 3D).

Cells were prepared for immunofluorescence as previously described. Briefly, cells were fixed using 3.7% paraformaldehyde for 30 min at room temperature and washed three times using PBS. The fixed cells were permeabilized with 0.1% Triton X-100 for 20 min and incubated with 1% BSA blocking solution at room temperature for 1 hour. Samples were incubated with either the antigen specific primary antibodies for the markers outlined in the text, followed by an appropriate secondary antibodies (Table 1), or with phalloidin (1:500; Molecular Probes) and DAPI (1:10,000; Molecular Probes). Both primary and secondary antibodies were diluted in antibody diluent (DAKO). The immunolabeled cells were examined using a fluorescent microscope (Olympus BX60) and imaged using a confocal microscope (Zeiss LSM 700 and LSM 780). Confocal z-stacks of 3D vascular networks were analyzed using Imaris 8.0 Filament software (Bitplane).

TABLE 1

List of antibodies and fluorophore-conjugated dyes.

| Antibody | Source | Catalog# | Purpose | Host Species and Reactivity | Concentration |
|---|---|---|---|---|---|
| AcLDL | Invitrogen | L-3484 | IF | ECs | 10 µg/mL |
| AlexaFluor 488 | Molecular Probe | A11008 | IF | Goat anti-rabbit | 1:1000 |
| CD 31 | Dako | M0823, clone JC10/A | IF | Mouse anti-human | 1:100 |
| CD 31-PE | BD | 555446 | FC | Mouse anti-human | 1:15 |
| DAPI | Roche | 10236276 | IF | Nuclei | 1:1000 |
| eNOS | BD | 610297 | IF | Mouse anti-human | 1:100 |
| ICAM-1-FITC | Sigma | F 0549 | FC | Mouse anti-human | 1:10 |
| IgG FITC | BD | 554679 | FC | Mouse anti-human | 1:15 |
| IgG-PE | BD | 555749 | FC | Mouse anti-human | 1:15 |
| PDGFRβ | Santa Cruz | SC-432 | IF | Rabbit anti-human | 1:200 |
| PDGFRβ-PE | BD | 558821 | FC | Mouse anti-human | 1:15 |
| AlexaFluor 488-Phalloidin | Molecular Probe | A12379 | IF | F-actin | 1:500 |
| VEcad | Santa Cruz | Sc-9989 | IF | Mouse anti-human | 1:200 |
| VEcad-FITC | BD | 560410 | FC | Mouse anti-human | 1:15 |
| VEcad-PE | BD | 560494 | FC | Mouse anti-human | 1:15 |
| vWF | Dako | M0616 Clone f8/86 | IF | Mouse anti-human | 1:200 |

Matrigel Cord Formation.

Cord formation on Matrigel was assessed as previously described. Briefly, Matrigel was cast into 16 well chamber slides (Lab-Tek). After polymerization, 15,000 cells were seeded per well in high VEGF media. Cord formation was observed after 4, 6 and 12 hours.

Tumor Necrosis Factor Alpha (TNFα) Response.

T1D-derived early ECs were magnetically sorted using VEcad-PE (Miltenyi Biotech). Sorted ECs were culture on in high VEGF media for an additional 6 days to mature. On the last day of maturation (day 18), high VEGF media was removed and sorted ECs were treated with 10 ng/mL TNFα in high VEGF media (Promocell) for 24 hours. The treated ECs were washed with PBS before dissociated to analyze ICAM-1-FITC (Sigma) expression using flow cytometry.

Acrylated hyaluronic acid (AHA) hydrogel and EVCs constructs. AHA hydrogels were prepared as previously reported. Briefly, AHA (3 wt %) was dissolved in a triethanolamine buffer solution (TEOA buffer, Sigma). The cell adhesive peptides (RGDS (SEQ ID NO: 3); GenScript) were dissolved in TEOA buffer and added to the AHA solution at final peptide concentrations of 3.7 mM (corresponding to 10% of available acrylate groups within 3 wt % AHA) and were allowed to react for one hour with gentle shaking. Recombinant human VEGF165 (R&D), bFGF (R&D), Ang-1 (R&D), tumor necrosis factor-alpha (TNF-α; R&D) and stromal cell-derived factor-1 (SDF-1; R&D) were added at 50 ng/mL into the AHA-RGDS mixture ("RGDS" disclosed as SEQ ID NO: 3). Following the resuspension of cells into this solution, MMP peptide crosslinker (MMP; GenScript) dissolved in TEOA buffer was added at 4.83 mM (corresponding to the 25% of available acrylate groups within the 3 wt % AHA). Derived EVCs were encapsulated in HA hydrogels at a density of 4×106 cells/mL and cultured for up to 3 days in endothelial growth media 2 (EGM2; Lonza). Visualization and image acquisition were performed using an inverted light microscope (Olympus) and confocal microscope (Zeiss LSM 700 and 780) along the culture.

Hypoxia-Inducible (HI) Hydrogels and EVCs Constructs.

HI hydrogels were prepared as previously reported. Briefly, gelatin and ferulic acid polymer solution (4 wt %) was dissolved in PBS (pH 7.4) and mixed with EVC pellets to provide cell suspension, and then laccase solution (100 U/mL) was added at a volume ratio of 3:1 (polymer solution: laccase solution) and gently mixed for 1 min at 37° C. The final concentration of the polymer, laccase and cells were 3 wt. %, 25 U/mL and 3×106 cells/mL, respectively. To generate hypoxic and non-hypoxic hydrogels, 45 µL and 90 µL cell mixture was added respectively to each well of a 96-well plate and allowed to react at 37° C. for 20 min. On top of the EVC encapsulated hypoxic and non-hypoxic hydrogels, endothelial cell growth media (Lonza) and a growth factor mix as described above for AHA hydrogels at 10 ng/mL was added at 200 µL and 100 µL, respectively. EVC encapsulated hydrogels were cultured under standard cell culture conditions (37° C. and 5% CO2) for up to 72 hours. The culture medium was replaced every 24 hours. EVC morphologies were observed using optical microscopy (in phase-contrast mode) and confocal microscopy (Zeiss LSM 780).

Statistics.

All analyses were performed in triplicate samples for at least n=3. Two-tailed t test was performed to determine significance. All graphs were drawn using GraphPad Prism 5. Significance levels were set at *p<0.05, p<0.01, and *p<0.001.

Cell Culture and Differentiation.

EVC differentiation from BC1 and T1D hiPSC lines followed our established protocols. Briefly, undifferentiated hiPSC (BC1 and T1D) were maintained on inactivated mouse embryonic fibroblast feeder layers in growth medium with 80 percent ES-EMEM/F12 (Global Stem), 20 percent serum replacement (Invitrogen), and 10 ng/ml basic fibroblast growth factor (bFGF). For differentiation, hiPSCs were collected through digestion with EDTA (Promega), single cells were seeded and plated onto collagen IV (Trevigen)-coated cell culture plates with a concentration of $5\times10^4$ cell/cm$^2$ supplemented with 10 µM ROCK inhibitor Y-27632 (Stemcell Technologies). Cells were cultured for 6 days in a differentiation medium composed of alpha-MEM (Invitrogen), 10% FBS (HyClone), and 0.1 mM β-mercaptoethanol (β-ME), with the medium changed daily. Differentiated cells were collected through digestion with TrypLE (Invitrogen) on day 6 and seeded at a concentration of $2\times10^4$ cells/cm$^2$ on collagen type IV-coated plates in endothelial cell growth media (ECGM) (PromoCell) supplemented with 2% FBS, 50 ng/mL VEGF with 10 µM SB431542 (Tocris) for 6 days. The medium was changed every other day. ECFCs (Lonza) were cultured under the manufacturer's protocol. Briefly, cells were seeded and expanded in endothelial growth media EGM-2 (Lonza) and cells with passages 6 through 8 were used for experiments.

Synthesis of Acrylated Hyaluronic Acid (AHA) Hydrogels Macromer.

AHA macromer synthesis was conducted as previously reported. In brief, AHA was synthesized in two steps: (1) the tetrabutyl-ammonium salt of HA (HA-TBA) was formed by reacting sodium hyaluronate (90 kDa, LifeCore Biomedical) with the ion exchange resin Dowex-100 (Sigma) and neutralized with 0.2M TBA-OF (Sigma); (2) acrylic acid (3 eq) and HA-TBA (1 eq) were coupled in the presence of dimethylaminopyridine (DMAP; 0.15 eq) and di-tert-butyl dicarbonate (3 eq) in DMSO, followed by dialysis and lyophilization. $^1$H NMR spectra were used to confirm the modification of the AHA. The cell-adhesive peptide GCGYGRGDSPG (SEQ ID NO: 1) (RGDS (SEQ ID NO: 3), molecular weight [MW]: 1025.1 Da) and MMP-sensitive peptide crosslinker GCRDGPQGWGQDRCG (SEQ ID NO: 2) (MMP, MW: 1754 Da) were purchased (Genscript, >95% purity per manufacturer HPLC analysis.)

Generation of Human Vascular Constructs from ECFCs and EVCs.

We engineered human vascular networks within the AHA hydrogels. AHA macromer was dissolved in triethanolamine buffered saline (TEOA buffer: 0.2M TEOA) at 3 wt %. Cell adhesive peptides (RGDS (SEQ ID NO: 3), GenScript) were dissolved in TEOA buffer and added to the AHA solution to the final peptide concentration of 4.8 mM Recombinant human VEGF165 (Pierce), bFGF (Invitrogen), Ang-1 (R&D Systems), TNF-alpha (R&D Systems), and stromal cell-derived factor-1 (SDF-1; R&D Systems) were also added into the AHA-RGD mixture at 50 ng/ml. The mixture was allowed to react for 1 hour with gentle shaking. For cross-linking, an MMP cross linker (MMP, GenScript) dissolved in TEOA buffer was added to a final concentration of 5.15 mM. ECFCs or EVCs were encapsulated in AHA hydrogels at a density of $5 \times 10^6$ cells/ml by suspending the cells in the AHA-RGD solution as described above prior to the addition of the MMP crosslinker. A 50 µl volume of the final mixture was pipetted into sterile molds (5 mm diameter, 2 mm height) and allowed to react for 10 minutes at room temperature in a laminar flow hood. The constructs were then cultured in ECFC culture media in the conditions described throughout the study. Cured AHA constructs without cells cultured in the same media and duration, served as acellular controls.

Streptozotocin (STZ) Induced Diabetic Immunodeficient Mice.

The standard protocol from the American Models of Diabetic Complications Consortium was used to induce diabetes in mice. Nude mice (nu/nu) at about 2-2.5 months of age (about 20-25 g body weight) were randomly assigned to a diabetic or a non-diabetic group. Animals in the diabetic group received 5 daily intraperitoneal injections of STZ at a dose of 50 mg/kg body weight (STZ is freshly dissolved in citrate buffer, pH 4.5). Prior to injection, mice were fasted for 4 to 6 hours. The weight and blood glucose of each mouse were checked daily for up to 2 weeks after the STZ injection. Successful induction of diabetes was confirmed by two consecutive blood glucose levels readings higher than 300 mg/dl over a 48-hour period. Blood glucose was measured using an Accuchek blood glucose meter (Roche) by obtaining 20-25 µl of blood from a tail vein puncture (30 gauge needle).

Full Thickness Diabetic Wound Mouse Model and Treatment with Acellular and Vascularized Constructs.

Full thickness diabetic wounds mouse model was constructed by incorporating various protocols from the literature. After induction of diabetes mellitus was confirmed, diabetic nude mice were anesthetized with isoflurane (Thermo Fisher). A depilatory was applied (Nair), prior to wound creation, to ensure better dressing adherence. Next, two full-thickness, 6 mm-diameter punch wounds were made using a biopsy punch (Integra) on each side of the posterior dorsum. Vascularized constructs, which were generated in vitro, were then transplanted into one side of the animal (one per wound). The time point was logged as day 0 post-wound. Betadine was applied around the periphery of the wound to enhance dressing adherence. The wound on the opposing side was left with no construct treatment. Both wounds were then covered with Tegaderm dressing (3M). Six to eight constructs were implanted for each group at each time point. At each time point of interest, as described below, human specific fluorescein-conjugated *Ulex europaeus I* (UEA-I) Lectin (1:10; Vector Laboratory) and mouse-specific rhodamine-conjugated Isolectin *Griffonia simplicifolia* (GS)-IB$_4$ (1:10; Invitrogen) were injected through the tail veins of the mice. After 30 minutes, the mice were euthanized, and the constructs were harvested and fixed in 3.7% formaldehyde (Sigma). The tissue was processed for immunohistochemistry or histology. The Johns Hopkins University Institutional Animal Care and Use Committee approved all animal protocols.

Bloodflow and Planetary Measurement.

During the study, the blood flow profiles inside the wounds were monitored noninvasively using moorFLPI speckle contrast imager (Moor Instruments, Inc.) as previously described. The measurements were normalized by the blood flow measurements of the adjacent healthy skin area. Photometric analysis of wound closure rate was done along with blood flow measurement.

Histology and Immunohistochemistry Analysis.

Following fixation of the explants, the samples were dehydrated in serial ethanol (70%-100%), embedded in paraffin, serially sectioned at 5 µm, and treated with hematoxylin and eosin (H&E) stain. Immunofluorescent stains of paraffin embedded tissue section were carried out with serial rehydration of ethanol (100%-80%) after xylene treatment. Following with antigen retrieval using retrieval solution (Dako) in pressure cooker for 25 minutes. Slides were then stained with Rabbit anti-mouse CD31 (1:100 Abcam), Goat anti-human IgG (1:100 Invitrogen) Along with anti-mouse Alexa Fluor 646 (1:250 Life Technologies), anti-rabbit Alexa Fluor 564 (1:250 Life Technologies) and counter stain with DAPI. Histological images were taken with an upright light microscope (Nikon Accuscope 3000) and a camera (Nikon DS-F12). Images were taken using Zeiss LSM780. At least 3 different sections s per condition and per time point were sampled. Images were sampled at least 8 different locations per slide for quantification near the wound area. Image analyses were done using Image J (NIH) using particles analyzer macro plug in.

Statistical Analysis and Regression Fit.

Statistical analysis was performed using GraphPad Prism 6.01 (GraphPad Software Inc.), A non-linear regression fit, One Way ANOVA with Tukey's posttest, or Two Way ANOVA with Bonferroni's post test were used where appropriate, in which significance levels were set at *$p<0.05$, $p<0.01$, and *$p<0.001$. Unless otherwise indicated, all graphical data are reported ±SEM.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method comprising the steps of:
   a) plating a single-cell suspension of human induced pluripotent stem cells (hiPSCs) from human subjects having Type-1 Diabetes (T1D) at a cell seeding density of $1\times10^5$ cells/cm$^2$ or greater on collagen-coated cell culture plates supplemented with Y-27632;
   b) culturing the cells from step a) in a differentiation medium;
   c) collecting differentiated cells and seeding the cells onto collagen coated plates in endothelial cell growth medium comprising VEGF and SB431542; and d) culturing the cells from c) until Early Vascular Cells (EVCs) are formed, wherein at least 47% of the EVCs express vascular endothelial cadherin (VEcad+ cells).

2. The method of claim 1 wherein the differentiation medium is a serum free culture medium.

3. The method of claim 1 further comprising:
culturing to 60-80% confluency; replacing the differentiation medium with serum free culture medium; and adding a GSK3 inhibitor CHIR99021 to the serum free culture medium.

4. The method of claim 1, wherein the EVCs comprise cells that express platelet derived growth factor β (PDGF β+ cells).

5. The method of claim 1, further comprising a step of encapsulating the EVCs of step d) in a hydrogel.

6. The method of claim 5, wherein the hydrogel is selected from the group consisting of hyaluronic acid (HA), collagen, or a combination thereof.

7. The method of claim 1, further comprising a step of encapsulating the EVCs of step d) in an oxygen-controllable and hypoxia-inducible hydrogel.

8. The method of claim 1, further comprising: step e) forming EVC vascular networks comprising endothelial cells and pericytes.

9. The method of claim 8, further comprising a step of encapsulating the EVCs of step d) in a hydrogel prior to forming the EVC networks comprising endothelial cells and pericytes.

10. The method of claim 9, wherein the hydrogel is selected from the group consisting of hyaluronic acid (HA), collagen, or a combination thereof.

11. The method of claim 8, further comprising a step of encapsulating the EVCs in an oxygen-controllable and hypoxia-inducible hydrogel.

12. The method of claim 9 wherein the EVC networks undergo vasculogenesis.

13. The method of claim 12 wherein the EVC networks form functional human microvascular networks.

14. The method of claim 8 further comprising the steps of:
administering the EVC networks comprising endothelial cells and pericytes to a wound of a subject; and
enhancing healing of the wound compared to a reference wound not administered the EVC networks comprising endothelial cells and pericytes.

15. The method of claim 14, wherein the EVC networks are administered by implantation into a diabetic wound in a diabetic subject and reestablish blood flow and improve wound healing rate when compared to a diabetic subject that has not been administered the EVC networks.

16. The method of claim 14, wherein the wound is a diabetic ulcer.

17. The method of claim 1, wherein the hiPSCs are derived from a patient with a HIF2α+ mutation.

18. The method of claim 1, wherein the differentiation medium comprises alpha MEM and beta-mercaptoethanol.

* * * * *